(12) United States Patent
Sundermann et al.

(10) Patent No.: US 6,998,409 B2
(45) Date of Patent: *Feb. 14, 2006

(54) SUBSTITUTED 2-PYRIDINE CYCLOHEXANE-1,4-DIAMINE COMPOUNDS

(75) Inventors: Bernd Sundermann, Aachen (DE); Corinna Sundermann, Aachen (DE); Helmut Buschmann, Esplugues de Llobregat (ES); Barbara Heller, Dettmannsdorf (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/704,200

(22) Filed: Nov. 10, 2003

(65) Prior Publication Data

US 2004/0147741 A1    Jul. 29, 2004

Related U.S. Application Data

(63) Continuation of application No. PCT/EP02/05078, filed on May 8, 2002.

(30) Foreign Application Priority Data

May 9, 2001    (DE) ................................ 101 23 163

(51) Int. Cl.
*A61K 31/4439* (2006.01)
*C07D 401/02* (2006.01)

(52) U.S. Cl. ..................... 514/339; 546/277.4; 546/85; 546/329; 514/292; 514/357

(58) Field of Classification Search ................. 514/339, 514/292, 357; 546/277.4, 85, 329
See application file for complete search history.

(56) References Cited

U.S. PATENT DOCUMENTS 4,113,866 A    9/1978 Lednicer

FOREIGN PATENT DOCUMENTS

WO    WO-99/36421 A1    7/1999
WO    WIPO- 01/87838    * 11/2001

OTHER PUBLICATIONS

Bertorelli, R. et al. "Nociceptin/orphanin FQ and Its receptor: a potential target for drug discovery" Trends in Pharmacological Sciences, 21(7) (2000), pp. 233-234.
International Search Report.
Abdulla and Smith, J. Neurosci., 18, 1998, p. 9685-9694.
Ardati et al. Mol. Pharmacol., 51, 1997, p. 816-824.
Calo et al., Br. J. Pharmacol., 129, 2000, 1261-1283.
Champion and Kadowitz, Biochem. Biophys. Res. Comm., 234, 1997, p. 309-312.
Conner et al., Br. J. Pharmacol. 118, 1996, p. 205-207.
Darland et al., Trends in Neurosciences, 21, 1998, p. 215-221.
Faber et al., Br. J. Pharmacol., 119, 1996, p. 189-190.
Gumusel et al., Life Sci., 60, 1997, p. 141-145.
Gutiérrez et al., Abstract 536.18, Society for Neuroscience, vol. 24, 28th Ann. Meeting, Los Angeles, Nov. 7-12, 1998.
Hara et al., Br. J. Pharmacol. 121, 1997, p. 401-408.
Jenck et al., Proc. Natl. Acad. Sci. USA 94, 1997, 14854-14858.
Kapusta et al., Life Sciences, 60, 1997, PL 15-21.
King et al., Neurosci. Lett., 223, 1997, 113-116.
Knoflach et al., J. Neuroscience 16, 1996, p. 6657-6664.
Manabe et al., Nature, 394, 1997, p. 577-581.
Matthes et al., Mol. Pharmacol. 50, 1996, p. 447-450.
Meunier et al., Nature 377, 1995, p. 532-535.
Mogil et al., Neurosci. Letters 214, 1996, p. 131-134.
Mogil et al., Neuroscience 75, 1996, p. 333-337.
Mollereau et al., FEBS Letters, 341, 1994, p. 33-38.
Nishi et al., EMBO J., 16, 1997, p. 1858-1864.
Pomonis et al., NeuroReport, 8, 1996, p. 369-371.
Reinscheid et al., Science 270, 1995, p. 792-794.
Sandin et al., Eur. J. Neurosci., 9, 1997, p. 194-197.
Shu et al., Neuropeptides, 32, 1998, 567-571.
Vaughan et al., Br. J. Pharmacol. 117, 1996, p. 1609-1611.
Xu et al., NeuroReport, 7, 1996, 2092-2094.
Yamamoto and Nozaki-Taguchi, Anesthesiology, 87, 1997.
Yamamoto et al., Neuroscience, 81, 1997, p. 249-254.

* cited by examiner

*Primary Examiner*—Charanjit S. Aulakh
(74) *Attorney, Agent, or Firm*—Crowell & Moring LLP

(57) ABSTRACT

Substituted 2-pyridine cyclohexane-1,4-diamine compounds, a method for their production, pharmaceutical compositions containing them, and the use of such substituted 2-pyridine cyclohexane-1,4-diamine compounds for treating pain and various other medical conditions.

57 Claims, No Drawings

SUBSTITUTED 2-PYRIDINE CYCLOHEXANE-1,4-DIAMINE COMPOUNDS

CROSS REFERENCE TO RELATED APPLICATIONS

This application is a continuation of international patent application no. PCT/EP02/05078, filed May 8, 2002, designating the United States of America, and published in German as WO 02/090330, the entire disclosure of which is incorporated herein by reference. Priority is claimed based on Federal Republic of Germany patent application no. DE 101 23 163.6, filed May 9, 2001.

BACKGROUND OF THE INVENTION

The present invention relates to substituted 2-pyridine cyclohexane-1,4-diamine compounds, to a process for their production, pharmaceutical compositions containing these compounds and to therapeutic uses of substituted 2-pyridine cyclohexane-1,4-diamine compounds.

The heptadecapeptide nociceptin is an endogenous ligand of the ORL1 (opioid receptor-like) receptor (Meunier et al., Nature 377, 1995, p. 532–535), which belongs to the family of opioid receptors and can be found in many regions of the brain and spinal cord (Mollereau et al., FEBS Letters, 341, 1994, p. 33–38, Darland et al., Trends in Neurosciences, 21, 1998, p. 215–221). The peptide is characterised by a high affinity, with a $K_d$ value of approximately 56 pM (Ardati et al., Mol. Pharmacol. 51, p. 816–824), and by a high selectivity for the ORL1 receptor. The ORL1 receptor is homologous to the $\mu$, $\kappa$ and $\delta$ opioid receptors and the amino acid sequence of the nociceptin peptide displays a strong similarity to those of the known opioid peptides. The nociceptin-induced activation of the receptor, via coupling with $G_{i/o}$ proteins, leads to an inhibition of adenylate cyclase (Meunier et al., Nature 377, 1995, p. 532–535). On a cellular level too there are functional similarities between the $\mu$, $\kappa$ and $\delta$ opioid receptors and the ORL1 receptor with regard to the activation of the potassium channel (Matthes et al., Mol. Pharmacol. 50, 1996, p. 447–450; Vaughan et al., Br. J. Pharmacol. 117, 1996, p. 1609–1611) and the inhibition of the L, N and P/Q type calcium channels (Conner et al., Br. J. Pharmacol. 118, 1996, p. 205–207; Knoflach et al., J. Neuroscience 16, 1996, p. 6657–6664).

After intracerebroventicular administration the nociceptin peptide displays a pronociceptive and hyperalgesic activity in various animal models (Reinscheid et al., Science 270, 1995, p. 792–794; Hara et al., Br. J. Pharmacol. 121, 1997, p. 401–408). These findings can be explained as inhibition of stress-induced analgesia (Mogil et al., Neurosci. Letters 214, 1996, p. 131–134; and Neuroscience 75, 1996, p. 333–337). In this connection an anxiolytic activity of nociceptin has also been demonstrated (Jenck et al., Proc. Natl. Acad. Sci. USA 94, 1997, 14854–14858).

On the other hand, an antinociceptive effect of nociceptin has also been demonstrated in various animal models, particularly after intrathecal administration. Nociceptin inhibits the activity of kainate- or glutamate-stimulated basal ganglia neurones (Shu et al., Neuropeptides, 32, 1998, 567–571) or glutamate-stimulated spinal cord neurones (Faber et al., Br. J. Pharmacol., 119, 1996, p. 189–190); it has an antinociceptive action in the tail flick test in mice (King et al., Neurosci. Lett., 223, 1997, 113–116), in the flexor reflex model in rats (Xu et al., NeuroReport, 7, 1996, 2092–2094) and in the formalin test in rats (Yamamoto et al., Neuroscience, 81, 1997, p. 249–254). An antinociceptive action of nociceptin has also been demonstrated in models for neuropathic pain (Yamamoto and Nozaki-Taguchi, Anesthesiology, 87, 1997), which is particularly interesting in as much as the activity of nociceptin increases after axotomy of the spinal nerves. This is in contrast to the classical opioids, whose activity decreases under these conditions (Abdulla and Smith, J. Neurosci., 18, 1998, p. 9685–9694).

Furthermore, the ORL1 receptor is also involved in the regulation of other physiological and pathophysiological processes. These include among others learning and memory development (Sandin et al., Eur. J. Neurosci., 9, 1997, p. 194–197; Manabe et al., Nature, 394, 1997, p. 577–581), hearing (Nishi et al., EMBO J., 16, 1997, p. 1858–1864), eating (Pomonis et al., NeuroReport, 8, 1996, p. 369–371), blood pressure regulation (Gumusel et al., Life Sci., 60, 1997, p. 141–145; Campion and Kadowitz, Biochem. Biophys. Res. Comm., 234, 1997, p. 309–312), epilepsy (Gutiérrez et al., Abstract 536.18, Society for Neuroscience, Vol. 24, 28$^{th}$ Ann. Meeting, Los Angeles, Nov. 7–12, 1998) and diuresis (Kapista et al., Life Sciences, 60, 1997, PL 15–21). An overview article by Calo et al. (Br. J. Pharmacol., 129, 2000, 1261–1283) gives an overview of the indications or biological processes in which the ORL1 receptor plays or with a high degree of probability could play a part. Those cited include: analgesia, stimulation and regulation of eating, influence on $\mu$-agonists such as morphine, treatment of withdrawal symptoms, reduction of the addiction potential of morphines, anxiolysis, modulation of motor activity, amnesia, epilepsy; modulation of neurotransmitter release, particularly of glutamate, serotonin and dopamine, and hence neurodegenerative diseases; influencing of the cardiovascular system, triggering of an erection, diuresis, antinatriuresis, ionic equilibrium, aterial blood pressure, water-storage disorders, intestinal motility (diarrhoea), relaxing effects on the respiratory tracts, micturation reflex (urinary incontinence). The use of agonists and antagonists as anoretics, analgesics (also in coadministration with opioids) or nootropics is also discussed.

The possible applications of compounds that bind to the ORL1 receptor and activate or inhibit it are correspondingly diverse.

SUMMARY OF THE INVENTION

The object of the present invention was to provide medicaments that act on the nociceptin/ORL1 receptor system and are therefore suitable as medicaments for the treatment of, in particular, the various diseases known in the art to be linked with this system or for treating indications associated with this receptor system.

The invention thus provides substituted 2-pyridine cyclohexane-1,4-diamine compounds corresponding to the formula I,

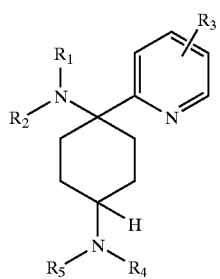

I wherein
  $R^1$ and $R^2$ are independently selected from H; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

or the radicals $R^1$ and $R^2$ together form a ring and denote $CH_2CH_2OCH_2CH_2$, $CH_2CH_2NR^6CH_2CH_2$ or $(CH_2)_{3-6}$, where $R^6$ is selected from H; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

$R^3$ is selected from H; $C_{1-8}$ alkyl, each being saturated or unsaturated, branched or unbranched, mono- or polysubstituted or unsubstituted; $C_{3-8}$ cycloalkyl, saturated or unsaturated, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted; SH, OH, F, Cl, I, Br, CN, $NO_2$, $OR^{26}$, $NR^{27}R^{28}$;

where $R^{26}$ is selected from $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl or heteroaryl, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH; aryl, $C_{3-8}$ cycloalkyl or heteroaryl bonded via $C_{1-3}$ alkyl, saturated or unsaturated, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH;

where $R^{27}$ and $R^{28}$ are independently selected from H, $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl or heteroaryl, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH; aryl, $C_{3-8}$ cycloalkyl or heteroaryl bonded via $C_{1-3}$ alkyl, saturated or unsaturated, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH;

or the radicals $R^{27}$ and $R^{28}$ together denote $CH_2CH_2OCH_2CH_2$, $CH_2CH_2NR^{29}CH_2CH_2$ or $(CH_2)_{3-6}$, where $R^{29}$ is selected from H, $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl or heteroaryl, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH; aryl, $C_{3-8}$ cycloalkyl or heteroaryl bonded via $C_{1-3}$ alkyl, saturated or unsaturated, each being unsubstituted or mono- or polysubstituted with F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and/or OH;

$R^4$ is selected from H, $C_{1-8}$ alkyl, saturated or unsaturated, branched or unbranched, mono- or polysubstituted or unsubstituted; or $C(X)R^7$, $C(X)NR^7R^8$, $C(X)OR^9$, $C(X)SR^9$, $S(O_2)$ $R^9$ where X=O or S, where $R^7$ is selected from H, $C_{1-8}$ alkyl or $C_{3-8}$ cycloalkyl, each being saturated or unsaturated, branched or unbranched, mono- or polysubstituted or unsubstituted; aryl, heteroaryl, each being unsubstituted or mono- or polysubstituted; aryl, $C_{3-8}$ cycloalkyl or heteroaryl bonded via a saturated or unsaturated, branched or unbranched, substituted or unsubstituted $C_{1-4}$ alkyl group, each being unsubstituted or mono- or polysubstituted;

where $R^8$ is selected from H, $C_{1-4}$ alkyl, saturated or unsaturated, branched or unbranched, mono- or polysubstituted or unsubstituted or the radicals $R^7$ and $R^8$ together form a ring and denote $CH_2CH_2OCH_2CH_2$, $CH_2CH_2NR^{10}CH_2CH_2$ or $(CH_2)_{3-6}$, where $R^{10}$ is selected from H; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

where $R^9$ is selected from $C_{1-8}$ alkyl or $C_{3-8}$ cycloalkyl, each being saturated or unsaturated, branched or unbranched, mono- or polysubstituted or unsubstituted; aryl, heteroaryl, each being unsubstituted or mono- or polysubstituted; aryl, $C_{3-8}$ cycloalkyl or heteroaryl bonded via a saturated or unsaturated, branched or unbranched, substituted or unsubstituted $C_{1-4}$ alkyl group, each being unsubstituted or mono- or polysubstituted;

$R^5$ is selected from $C_{3-8}$ cycloalkyl, aryl or heteroaryl, each being unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=O, S or $H_2$, where $R^{11}$ is selected from H, $C_{1-7}$ alkyl, saturated or unsaturated, branched or unbranched, mono- or polysubstituted or unsubstituted; or $C(O)O$—$C_{1-6}$ alkyl, saturated or unsaturated, branched or unbranched, mono- or polysubstituted or unsubstituted;

and where $R^{12}$ is selected from

H; $C_{3-8}$ cycloalkyl, aryl or heteroaryl, each being unsubstituted or mono- or polysubstituted, or $R^4$ and $R^5$ together form a heterocyclic compound with between 3 and 8 atoms in the ring, saturated or unsaturated; mono- or polysubstituted or unsubstituted, which can optionally be condensed with other rings, optionally in the form of their racemates, their pure stereoisomers, in particular enantiomers or diastereomers, or in the form of mixtures of stereoisomers, in particular enantiomers or diastereomers, in any mixing ratio;

in the form described or in the form of their acids or their bases or in the form of their salts, in particular the physiologically compatible salts or salts of physiologically compatible acids or cations; or in the form of their solvates, in particular hydrates.

All these compounds or groups of compounds according to the invention display outstanding binding to the ORL1 receptor.

Within the meaning of this invention alkyl or cycloalkyl radicals are understood to be saturated and unsaturated (but not aromatic), branched, unbranched and cyclic hydrocarbons, which can be unsubstituted or mono- or polysubstituted. $C_{1-2}$ alkyl stands for C1 or C2 alkyl, $C_{1-3}$ alkyl for C1, C2 or C3 alkyl, $C_{1-4}$ alkyl for C1, C2, C3 or C4 alkyl, $C_{1-5}$ alkyl for C1, C2, C3, C4 or C5 alkyl, $C_{1-6}$ alkyl for C1, C2, C3, C4, C5 or C6 alkyl, $C_{1-7}$ alkyl for C1, C2, C3, C4, C5, C6 or C7 alkyl, $C_{1-8}$ alkyl for C1, C2, C3, C4, C5, C6, C7 or C8 alkyl, $C_{1-10}$ alkyl for C1, C2, C3, C4, C5, C6, C7, C8, C9 or C10 alkyl and $C_{1-18}$ alkyl for C1, C2, C3, C4, C5, C6, C7, C8, C9, C10, C11, C12, C13, C14, C15, C16, C17 or C18 alkyl. Further, $C_{3-4}$ cycloalkyl stands for C3 or C4 cycloalkyl, $C_{3-5}$ cycloalkyl for C3, C4 or C5 cycloalkyl, $C_{3-6}$ cycloalkyl for C3, C4, C5 or C6 cycloalkyl, $C_{3-7}$ cycloalkyl for C3, C4, C5, C6 or C7 cycloalkyl, $C_{3-8}$ cycloalkyl for C3, C4, C5, C6, C7 or C8 cycloalkyl, $C_{4-5}$ cycloalkyl for C4 or C5 cycloalkyl, $C_{4-6}$ cycloalkyl for C4, C5 or C6 cycloalkyl, $C_{4-7}$ cycloalkyl for C4, C5, C6 or C7 cycloalkyl, $C_{-5-6}$ cycloalkyl for C5 or C6 cycloalkyl and $C_{5-7}$ cycloalkyl for C5, C6 or C7 cycloalkyl. With regard to cycloalkyl, the term also includes saturated cycloalkyls, in which one or 2 carbon atoms are replaced by a heteroatom, S, N or O. However, the term cycloalkyl also includes in particular mono- or polyunsaturated, preferably monounsaturated cycloalkyls with no heteroatom in the ring, provided that the cycloalkyl is not an aromatic system. The alkyl or cycloalkyl radicals are preferably methyl, ethyl, vinyl (ethenyl), propyl, allyl (2-propenyl), 1-propynyl, methyl ethyl, butyl, 1-methyl propyl, 2-methyl propyl, 1,1-dimethyl ethyl, pentyl, 1,1-dimethyl propyl, 1,2-dimethyl propyl, 2,2-dimethyl propyl, hexyl, 1-methyl pentyl, cyclopropyl, 2-methyl cyclopropyl, cyclopropyl methyl, cyclobutyl, cyclopentyl, cyclopentyl methyl, cyclohexyl, cycloheptyl, cyclooctyl, but also adamantyl, $CHF_2$, $CF_3$ or $CH_2OH$ and pyrazolinone, oxopyrazolinone, [1,4]dioxan or dioxolane.

In connection with alkyl and cycloalkyl, within the meaning of this invention the term substituted¦unless expressly defined otherwise¦refers to the substitution of at least one (optionally also several) hydrogen radicals by F, Cl, Br, I, $NH_2$, SH or OH, "polysubstituted" or "substituted" in the case of multiple substitution meaning that substitution takes place more than once both at different and also at the same atoms with the same or different substituents, for example three times at the same C atom as in the case of $CF_3$ or at various sites as in the case of —CH(OH) —CH═CH—CHCl$_2$. Particularly preferred substituents in this context are F, Cl and OH. With regard to cycloalkyl the hydrogen radical can also be replaced by $OC_{1-3}$ alkyl or $C_{1-3}$ alkyl (each being mono- or polysubstituted or unsubstituted), in particular methyl, ethyl, n-propyl, i-propyl, $CF_3$, methoxy or ethoxy.

The term $(CH_2)_{3-6}$ means —CH$_2$—CH$_2$—CH$_2$, —CH$_2$—CH$_2$—CH$_2$—CH$_2$, —CH$_2$—CH$_2$—CH$_2$—CH$_2$—CH$_2$— and CH$_2$—CH$_2$—CH$_2$—CH$_2$—CH$_2$—CH$_2$, $(CH_2)_{1-4}$ means —CH$_2$—, —CH$_2$—CH$_2$—, —CH$_2$—CH$_2$—CH$_2$— and —CH$_2$—CH$_2$—CH$_2$—CH$_2$—, $(CH_2)_{4-5}$ means —CH$_2$—CH$_2$—CH$_2$—CH$_2$— and —CH$_2$—CH$_2$—CH$_2$—CH$_2$—CH$_2$—, etc.

An aryl radical refers to ring systems with at least one aromatic ring but without heteroatoms in even just one of the rings. Examples include phenyl, naphthyl, fluoranthenyl, fluorenyl, tetralinyl or indanyl, in particular 9H-fluorenyl or anthracenyl radicals, which can be unsubstituted or mono- or polysubstituted.

A heteroaryl radical refers to heterocyclic ring systems with at least one unsaturated ring, which contain one or more heteroatoms selected from the group consisting of nitrogen, oxygen and/or sulfur and can also be mono- or polysubstituted. From the group of heteroaryls, furan, benzofuran, thiophene, benzothiophene, pyrrole, pyridine, pyrimidine, pyrazine, quinoline, isoquinoline, phthalazine, benzo[1,2,5] thiadiazole, benzothiazole, indole, benzotriazole, benzodioxolane, benzodioxan, carbazole, indol and quinazoline can be cited by way of example.

In connection with aryl and heteroaryl the term substituted refers to substitution of the aryl or heteroaryl with $R^{22}$, $OR^{22}$, a halogen, preferably F and/or Cl, a $CF_3$, a CN, an $NO_2$, an $NR^{23}R^{24}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene.

In this context the radical $R^{22}$ stands for H, a $C_{1-10}$ alkyl, preferably a $C_{1-6}$ alkyl, an aryl or heteroaryl or for an aryl or heteroaryl radical bonded via $C_{1-3}$ alkyl, saturated or unsaturated, or via a $C_{1-3}$ alkylene group, wherein these aryl and heteroaryl radicals may not themselves be substituted with aryl or heteroaryl radicals, the radicals $R^{23}$ and $R^{24}$, which are the same or different, denote H, a $C_{1-10}$ alkyl, preferably a $C_{1-6}$ alkyl, an aryl, a heteroaryl or an aryl or heteroaryl radical bonded via $C_{1-3}$ alkyl, saturated or unsaturated, or via a $C_{1-3}$ alkylene group, wherein these aryl and heteroaryl radicals may not themselves be substituted with aryl or heteroaryl radicals, or the radicals $R^{23}$ and $R^{24}$ together denote $CH_2CH_2OCH_2CH_2$, $CH_2CH_2NR^{25}CH_2CH_2$ or $(CH_2)_{3-6}$, and the radical $R^{25}$ stands for H, a $C_{1-10}$ alkyl, preferably a $C_{1-6}$ alkyl, an aryl or heteroaryl radical or for an aryl or heteroaryl radical bonded via $C_{1-3}$ alkyl, saturated or unsaturated, or via a $C_{1-3}$ alkylene group, wherein these aryl and heteroaryl radicals may not themselves be substituted with aryl or heteroaryl radicals.

The term salt refers to any form of the active ingredient according to the invention in which it assumes an ionic form or is charged and is coupled with a counterion (a cation or anion) or is in solution. This also includes complexes of the active ingredient with other molecules and ions, in particular complexes that are complexed via ionic interactions. In particular (and this is also a preferred embodiment of this invention) it refers to physiologically compatible salts, particularly physiologically compatible salts with cations or bases and physiologically compatible salts with anions or acids or a salt formed with a physiologically compatible acid or a physiologically compatible cation.

Within the meaning of this invention the term "physiologically compatible salt with anions or acids" is understood to mean salts of at least one of the compounds according to the invention¦generally protonated, for example on nitrogen¦as a cation with at least one anion, which are physiologically¦particularly in applications in humans and/or mammals¦compatible. Within the meaning of this invention this is understood to mean in particular the salt formed with a physiologically compatible acid, namely salts of the particular active ingredient with inorganic or organic acids which are physiologically—particularly in applications in humans and/or mammals—compatible. Examples of physiologically compatible salts of specific acids are salts of: hydrochloric acid, hydrobromic acid, sulfuric acid, methane sulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro1b6-benzo[d]isothiazol-3-one (saccharinic acid), monomethyl sebacic acid, 5-oxoproline, hexane-1-sulfonic acid, nicotinic acid, 2-, 3- or 4-aminobenzoic acid, 2,4,6-trimethyl benzoic acid, a-liponic acid, acetyl glycine, acetyl salicylic acid, hippuric acid and/or aspartic acid. The hydrochloride salt is particularly preferred.

Within the meaning of this invention the term "salt formed with a physiologically compatible acid" is understood to mean salts of the particular active ingredient with inorganic or organic acids which are physiologically—particularly in applications in humans and/or mammals—compatible. Hydrochloride is particularly preferred. Examples of physiologically compatible acids are: hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d] isothiazol-3-one (saccharinic acid), monomethyl sebacic acid, 5-oxoproline, hexane-1-sulfonic acid, nicotinic acid, 2-, 3- or 4-aminobenzoic acid, 2,4,6-trimethyl benzoic acid, α-liponic acid, acetyl glycine, acetyl salicylic acid, hippuric acid and/or aspartic acid.

Within the meaning of this invention the term "physiologically compatible salt with cations or bases" is understood to mean salts of at least one of the compounds according to the invention¦generally a (deprotonated) acid¦as anion with at least one, preferably inorganic, cation, which are physiologically¦particularly in applications in humans and/or mammals¦compatible. Particularly preferred are the salts of alkali and alkaline-earth metals but also $NH_4^+$, but particularly (mono-) or (di-) sodium, (mono-) or (di-) potassium, magnesium or calcium salts.

Within the meaning of this invention the term "salt formed with a physiologically compatible cation" is understood to mean at least one of the relevant compounds as anion with at least one inorganic cation, which is physiologically—particularly in applications in humans and/or mammals—compatible. Particularly preferred are the salts of alkali and alkaline earth metals but also $NH_4^+$, but particularly (mono-) or (di-) sodium, (mono-) or (di-) potassium, magnesium or calcium salts.

In one preferred embodiment the substituted 2-pyridine cyclohexane-1,4-diamine compounds are synthesised in such a way that according to formula I
$R^1$ and $R^2$ are independently selected from H; $C_{1-8}$ alkyl, saturated or unsaturated, branched or unbranched, mono- or polysubstituted or unsubstituted;
or the radicals $R^1$ and $R^2$ together form a ring and denote $CH_2CH_2OCH_2CH_2$, $CH_2CH_2NR^6CH_2CH_2$ or $(CH_2)_{3-6}$,
where $R^6$ is selected from H; $C_{1-8}$ alkyl, saturated or unsaturated, branched or unbranched, mono- or polysubstituted or unsubstituted, preferably
$R^1$ and $R^2$ are independently selected from H; $C_{1-4}$ alkyl, saturated or unsaturated, branched or unbranched, mono- or polysubstituted or unsubstituted;
or the radicals $R^1$ and $R^2$ together form a ring and denote $(CH_2)_{4-5}$, in particular
$R^1$ and $R^2$ are independently selected from methyl or ethyl or the radicals $R^1$ and $R^2$ together form a ring and denote $(CH_2)_5$.

In a preferred embodiment the substituted 2-pyridine cyclohexane-1,4-diamine compounds are synthesised in such a way that according to formula I
$R^3$ is selected from H; $C_{1-8}$ alkyl, each being saturated or unsaturated, branched or unbranched, mono- or polysubstituted or unsubstituted; $C_{3-8}$ cycloalkyl, saturated or unsaturated, mono-or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted; SH, OH, F, Cl, I, Br, CN, $NO_2$, $NH_2$, $OR^{26}$;
where $R^{26}$ is selected from $C_{1-6}$ alkyl, saturated or unsaturated, branched or unbranched, mono- or polysubstituted or unsubstituted;

preferably
$R^3$ is selected from H; $C_{1-6}$ alkyl, each being saturated or unsaturated, branched or unbranched, mono- or polysubstituted or unsubstituted; SH, OH, F, Cl, I, Br, CN, $NO_2$, $NH_2$, $OR^{26}$;
where $R^{26}$ is selected from $C_{1-6}$ alkyl, saturated or unsaturated, branched or unbranched, mono- or polysubstituted or unsubstituted;

in particular
$R^3$ is selected from H.

In another preferred embodiment the substituted 2-pyridine cyclohexane-1,4-diamine compounds are synthesised in such a way that according to formula I
$R^4$ is selected from H, $C(X)R^7$, $C(X)NR^7R^8$, $C(X)OR^9$, $C(X)SR^9$ or $S(O_2)R^9$ where X=O or S, preferably
$R^4$ is selected from H, $C(X)R^7$, $C(X)NR^7R^8$ or $C(X)OR^9$ where X=O, in particular
$R^4$ is selected from H or $C(O)R^7$; preferably with $R^7$ selected from
H; or $C_{1-8}$ alkyl, saturated or unsaturated, branched or unbranched, mono- or polysubstituted or unsubstituted;
preferably
H; or $C_{1-3}$ alkyl, saturated, unsubstituted, branched or unbranched;
in particular $CH_3$.

In a further preferred embodiment the substituted 2-pyridine cyclohexane-1,4-diamine compounds are synthesised in such a way that according to formula I
$R^4$ and $R^5$ together form a heterocyclic compound with between 3 and 8 atoms in the ring, saturated or unsaturated; mono- or polysubstituted or unsubstituted, preferably with between 5 and 7 atoms in the ring, of which in addition to the obligatory N, 0 to 1 other heteroatoms, selected from N, S or O, are in the ring;
wherein the heterocyclic compound formed by $R^4$ and $R^5$ together can optionally be condensed with other rings,
preferably with aromatic and/or heteroaromatic rings, wherein these can be condensed with other aromatic and/or heteroaromatic rings, in particular the heterocyclic compound formed by $R^4$ and $R^5$ together is condensed with one or two other rings, the heterocyclic compound formed by $R^4$ and $R^5$ together is preferably condensed with two other rings in such a way that $R^4$ and $R^5$ together denote

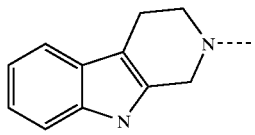

In yet another preferred embodiment the substituted 2-pyridine cyclohexane-1,4-diamine compounds are synthesised in such a way that according to formula I $R^4$ is selected from H or $C_{1-8}$ alkyl, saturated or unsaturated, branched or unbranched, mono- or polysubstituted or unsubstituted, preferably H or $C_{1-6}$ alkyl, saturated or unsaturated, branched or unbranched, mono- or polysubstituted or unsubstituted, in particular H or $C_{1-3}$ alkyl, saturated, unbranched and unsubstituted.

In a still further preferred embodiment the substituted 2-pyridine cyclohexane-1,4-diamine compounds are synthesised in such a way that according to formula I $R^5$ is selected from $C_{3-8}$ cycloalkyl, aryl or heteroaryl, each being unsubstituted or mono- or polysubstituted;

preferably $R^5$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each being unsubstituted or mono- or polysubstituted;

in particular $R^5$ is selected from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each being unsubstituted or mono- or polysubstituted.

In a further particularly preferred embodiment the substituted 2-pyridine cyclohexane-1,4-diamine compounds are synthesised in such a way that according to formula I $R^5$ is selected from $-CHR^{11}R^{12}$, $-CHR^{11}-CH_2R^{12}$, $-CHR^{11}-CH_2-CH_2R^{12}$, $-CHR^{11}-CH_2-CH_2-CH_2R^{12}$, $-C(Y)R^{12}$, $-C(Y)-CH_2R^{12}$, $-C(Y)-CH_2-CH_2R^{12}$ or $-C(Y)-CH_2-CH_2-CH_2R^{12}$ where $Y=O$, S or $H_2$, preferably $R^5$ is selected from $-CHR^{11}R^{12}$, $-CHR^{11}-CH_2R^{12}$, $-CHR^{11}-CH_2-CH_2R^{12}$, $-C(Y)R^{12}$, $-C(Y)-CH_2R^{12}$ or $-C(Y)-CH_2-CH_2R^{12}$ where $Y=O$ or S, in particular $R^5$ is selected from $-CHR^{11}R^{12}$, $-CHR^{11}-CH_2R^{12}$, $-CHR^{11}-CH_2-CH_2R^{12}$, $-C(Y)R^{12}$ or $-C(Y)-OH_2R^{12}$ where $Y=O$.

With regard to this embodiment it is particularly preferable if $R^{11}$ is selected from H, $C_{1-4}$ alkyl, saturated or unsaturated, branched or unbranched, mono- or polysubstituted or unsubstituted; or $C(O)O-C_{1-4}$ alkyl, saturated or unsaturated, branched or unbranched, mono- or polysubstituted or unsubstituted;

preferably

H, $C_{1-4}$ alkyl, saturated or unsaturated, branched or unbranched, mono- or polysubstituted or unsubstituted; or $C(O)O-C_{1-2}$ alkyl, saturated, unbranched, mono- or polysubstituted or unsubstituted;

in particular

H, $CH_3$, $C_2H_5$ and $C(O)O-CH_3$ and/or it is just as particularly preferable if $R^{12}$ is selected from $C_{3-8}$ cycloalkyl, aryl or heteroaryl, each being unsubstituted or mono- or polysubstituted;

preferably $R^{12}$ is selected from cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl, each being unsubstituted or mono- or polysubstituted;

in particular $R^{12}$ is selected from cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, each being unsubstituted or mono- or polysubstituted.

Furthermore the substituted 2-pyridine cyclohexane-1,4-diamine compounds according to the invention are particularly preferably selected from the following group:

N-(4-dimethylamino-4-pyridin-2-yl cyclohexyl)-N-[2-(1H-indol-3-yl)ethyl] acetamide dihydrochloride, non-polar diastereoisomer N'-[2-(1H-indol-3-yl)ethyl]-N,N-dimethyl-1-pyridin-2-yl cyclohexane-1,4-diamine trihydrochloride, non-polar diastereoisomer N'-[2-(1H-indol-3-yl)ethyl]-N,N-dimethyl-1-pyridin-2-yl cyclohexane-1,4-diamine trihydrochloride, polar diastereoisomer (S)-2-(4-dimethylamino-4-pyridin-2-yl cyclohexylamino)-3-(1H-indol-3-yl) methyl propionate trihydrochloride, non-polar diastereoisomer (S)-2-(4-dimethylamino-4-pyridin-2-yl cyclohexylamino)-3-(1H-indol-3-yl) methyl propionate trihydrochloride, polar diastereoisomer (S)-2-(4-dimethylamino-4-pyridin-2-yl cyclohexylamino)-3-(1H-indol-3-yl) propionic acid dihydrochloride, non-polar diastereoisomer, optionally also in the form of their racemates, the cited or other pure stereoisomers, in particular enantiomers or diastereomers, or in the form of mixtures of stereoisomers, in particular enantiomers or diastereomers, in any mixing ratio; optionally also in the form of acids or bases or in the form of other salts, particularly physiologically compatible salts or salts of physiologically compatible acids or cations; or in the form of their solvates, in particular hydrates.

The substances according to the invention are non-toxic, so they are suitable as a pharmaceutical active ingredient in medicaments.

The invention therefore also provides pharmaceutical compositions containing at least one substituted 2-pyridine cyclohexane-1,4-diamine compound according to the invention, optionally in the form of its racemate, pure stereoisomers, in particular enantiomers or diastereomers, or in the form of mixtures of stereoisomers, in particular enantiomers or diastereomers, in any mixing ratio; in the form described or in the form of its acids or its bases or in the form of its salts, in particular the physiologically compatible salts or salts of physiologically compatible acids or cations; or in the form of its solvates, in particular hydrates, and optionally containing suitable additives and/or auxiliary substances and/or optionally other active ingredients.

In addition to at least one substituted 2-pyridine cyclohexane-1,4-diamine compound according to the invention, the medicaments according to the invention optionally contain suitable additives and/or auxiliary substances, such as supporting materials, fillers, solvents, diluents, dyes and/or binders and can be administered as liquid dosage forms in the form of injection solutions, drops or linctuses, as semi-solid dosage forms in the form of granules, tablets, pellets, patches, capsules, plasters or aerosols. The choice of auxiliary substances, etc., and the amounts of them to be used depend on whether the medicament is to be administered by the oral, peroral, parenteral, intravenous, intraperitoneal, intradermal, intramuscular, intranasal, buccal or rectal route or locally, for example onto the skin, the mucous membranes or into the eyes. Preparations in the form of tablets, pastilles, capsules, granules, drops, linctuses and syrups are suitable for oral administration, solutions, suspensions, readily reconstitutable dry preparations and sprays for parenteral, topical and inhalative administration. Substituted 2-pyridine cyclohexane-1,4-diamine compounds according to the invention in a depot injection, in dissolved form or in a plaster, optionally with addition of agents promoting skin penetration, are preparations that are suitable for percutaneous administration. Preparation forms that can be used for oral or percutaneous administration can release the substituted 2-pyridine cyclohexane-1,4-diamine compounds according to the invention on a delayed basis. In principle other additional active ingredients known to the person skilled in the art can be added to the pharmaceutical compositions of the invention.

The amount of active ingredient to be administered to the patient varies according to the weight of the patient, the form of administration, the indication and the severity of the disease. Conventionally 0.005 to 1000 mg/kg, preferably 0.05 to 5 mg/kg, of at least one substituted 2-pyridine cyclohexane-1,4-diamine compound according to the invention is administered.

For all above forms of the pharmaceutical compositions according to the invention, it is particularly preferable if in addition to at least one substituted 2-pyridine cyclohexane-1,4-diamine compound the pharmaceutical composition also contains an opioid, preferably a strong opioid, in particular morphine, or an anaesthetic, preferably hexobarbital or halothane.

In a preferred form of the pharmaceutical composition, a substituted 2-pyridine cyclohexane-1,4-diamine compound according to the invention contained therein is present as a pure diastereomer and/or enantiomer, as a racemate or as a non-equimolar or equimolar mixture of diastereomers and/or enantiomers.

As can be read in the introduction with regard to the prior art, the ORL1 receptor has been identified in particular in the occurrence of pain. Accordingly, substituted 2-pyridine cyclohexane-1,4-diamine compounds according to the invention can be used for the treatment of pain, in particular of acute, neuropathic or chronic pain.

The invention therefore also embraces the use of substituted 2-pyridine cyclohexane-1,4-diamine compounds according to the invention; optionally in the form of their racemates, their pure stereoisomers, in particular enantiomers or diastereomers, or in the form of mixtures of stereoisomers, in particular enantiomers or diastereomers, in any mixing ratio; in the form described or in the form of their acids or their bases or in the form of their salts, in particular the physiologically compatible salts or salts of physiologically compatible acids or cations; or in the form of their solvates, in particular hydrates; for the treatment of pain, in particular of acute, neuropathic or chronic pain.

As already noted above, in addition to its function in the occurrence of pain the ORL1 receptor also plays a role in many other physiological processes of medical relevance in particular, so the invention also embraces the use of substituted 2-pyridine cyclohexane-1,4-diamine compounds according to the invention, optionally in the form of their racemates, their pure stereoisomers, in particular enantiomers or diastereomers, or in the form of mixtures of stereoisomers, in particular enantiomers or diastereomers, in any mixing ratio; in the form described or in the form of their acids or their bases or in the form of their salts, in particular the physiologically compatible salts or salts of physiologically compatible acids or cations; or in the form of their solvates, in particular hydrates; for the treatment of anxiety conditions, stress and stress-related syndromes, depression, epilepsy, Alzheimer's disease, senile dementia, general cognitive disfunctions, learning and memory difficulties (as a nootropic), withdrawal symptoms, alcohol and/or drug and/or medication abuse and/or dependency, sexual dysfunctions, cardiovascular diseases, hypotension, hypertension, tinnitus, pruritus, migraines, hearing difficulties, deficient intestinal motility, eating disorders, anorexia, obesity, locomotive disorders, diarrhoea, cachexia, urinary incontinence or for use as a muscle relaxant, anticonvulsive agent or anaesthetic or for coadministration in treatment with an opioid analgesic or with an anaesthetic, for diuresis or antinatriuresis and/or anxiolysis.

In the above applications it can be advantageous if a substituted 2-pyridine cyclohexane-1,4-diamine compound that is used is present as a pure diastereomer and/or enantiomer, as a racemate or as a non-equimolar or equimolar mixture of diastereomers and/or enantiomers.

The present invention also provides a process for the treatment, in particular in one of the above indications, of a non-human mammal or human requiring treatment for pain, in particular chronic pain, by administration of a therapeutically effective dose of a substituted 2-pyridine cyclohexane-1,4-diamine compound according to the invention or of a medicament according to the invention.

The invention also provides a process for the production of the substituted 2-pyridine cyclohexane-1,4-diamine compounds according to the invention as set out in the description and the following examples.

Particularly suitable is a process for the production of a substituted 2-pyridine cyclohexane-1,4-diamine compound according to the invention corresponding to formula I where $R^3$=H, referred to below as main process A, comprising the following steps:

a. a cyclohexane-1,4-dione protected with groups $S^1$ and $S^2$ according to formula II is reacted in the presence of a compound having the formula $HNR^{01}R^{02}$ with a cyanide, preferably potassium cyanide, to give a protected N-substituted 1-amino-4-oxocyclohexane carbonitrile compound according to formula III;

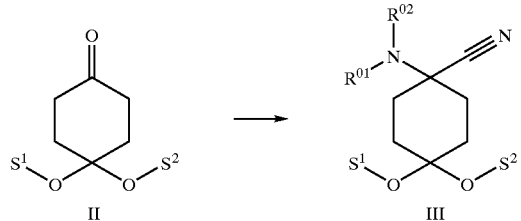

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, b. the aminonitrile according to formula III is brought into contact with cyclopentadienyl cycloocta-1,5-diene cobalt (I) [cpCo(cod)] and irradiated under acetylene, such that a compound according to formula IVa is produced;

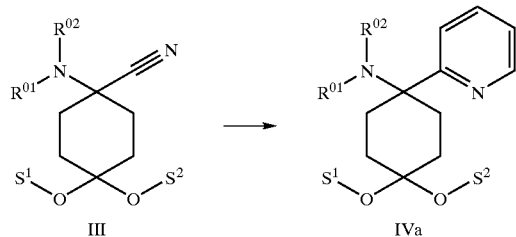

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, c. the protective groups $S^1$ and $S^2$ are eliminated at the compound according to formula IVa such that a tetrasubstituted 4-aminocyclohexanone compound according to formula IV is produced;

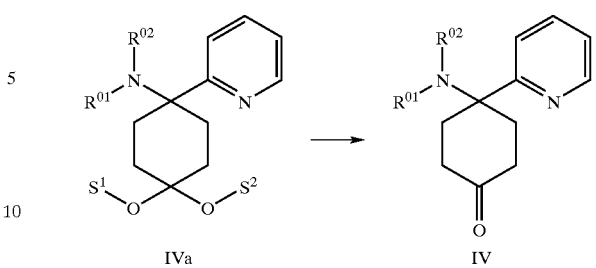

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, d. the tetrasubstituted 4-aminocyclohexanone compound according to formula IVa is reductively aminated with a compound having the formula $HNR^{04}R^{05}$ such that a 2-pyridine cyclohexane-1,4-diamine compound according to formula V is produced;

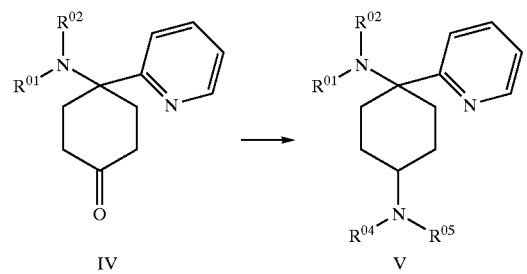

acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}$=H, a protective group is introduced at least once and acylation, alkylation or sulfonation optionally performed, until a compound according to formula I is produced, wherein $R^1$, $R^2$, $R^4$ and $R^5$ have the meaning given for the compounds according to the invention according to formula I and $R^{01}$ and $R^{02}$ are independently selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

$R^{04}$ is selected from H, H provided with a protective group; $C_{1-8}$ alkyl, saturated or unsaturated, branched or unbranched, mono- or polysubstituted or unsubstituted;

$R^{05}$ is selected from H, H provided with a protective group; $C_{3-8}$ cycloalkyl, aryl or heteroaryl, each being unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11'}$—$CH_2$—$CH_2$—$CH^2R^{12}$, —$C(Y)R_{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where $Y=H_2$, where $R^{11}$ is selected from H, $C_{1-7}$ alkyl, saturated or unsaturated, branched or unbranched, mono- or polysubstituted or unsubstituted;

and where $R^{12}$ is selected from

H; $C_{3-8}$ cycloalkyl, aryl or heteroaryl, each being unsubstituted or mono- or polysubstituted, or $R^{04}$ and $R^{05}$ together form a heterocyclic compound with between 3 and 8 atoms in the ring, saturated or unsaturated; mono- or polysubstituted or unsubstituted, and $S^1$ and $S^2$ are independently selected from protective groups or together denote a protective group, preferably monoacetal.

Particularly suitable is a process for the production of a substituted 2-pyridine cyclohexane-1,4-diamine compound according to the invention according to formula I where $R^3=H$, referred to below as alternative process A, comprising the following steps:

a. a cyclohexane-1,4-dione protected with groups $S^1$ and $S^2$ according to formula II is reductively aminated with a compound having the formula $HNR^{04}R^{05}$ such that a 4-aminocyclohexanone compound according to formula VI is produced;

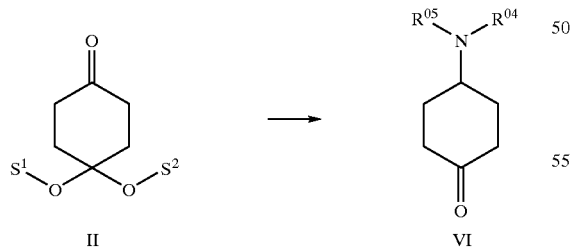

acylation, alkylation or sulfonation is then optionally performed in any sequence and optionally more than once and/or in the case of compounds where $R^{04}$ and/or $R^{05}=H$ protected by a protective group, a protective group is eliminated at least once and acylation, alkylation or sulfonation optionally performed and/or in the case of compounds where $R^{04}$ and/or $R^{05}=H$, a protective group is introduced at least once and acylation, alkylation or sulfonation optionally performed, b. the 4-aminocyclohexanone compound according to formula VI is reacted in the presence of a compound having the formula $HNR^{01}R^{02}$ with cyanide, preferably potassium cyanide, to give a cyclohexanone nitrile compound having formula VII,

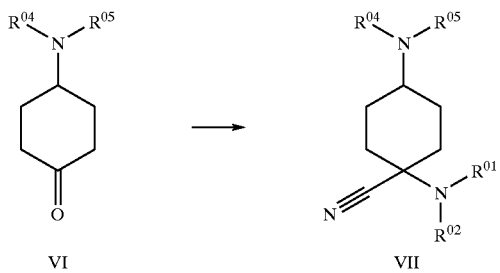

acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}=H$ protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}=H$, a protective group is introduced at least once and acylation, alkylation or sulfonation optionally performed, c. the cyclohexanone nitrile compound having formula VII is brought into contact with cyclopentadienyl cycloocta-1,5-diene cobalt (I) [cpCo(cod)] and irradiated under acetylene, such that a 2-pyridine cyclohexane-1,4-diamine compound according to formula V is produced,

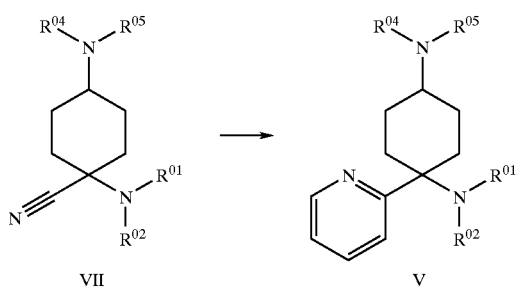

acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}=H$ protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}=H$, a protective group is introduced at least once and acylation, alkylation or sulfonation optionally performed, until a compound according to formula I is produced, wherein $R^1$, $R^2$, $R^4$ and $R^5$ have the meaning given for the compounds according to the invention according to formula I and $R^{01}$ and $R^{02}$ are independently selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

$R^{04}$ is selected from H, H provided with a protective group; $C_{1-8}$ alkyl, saturated or unsaturated, branched or unbranched, mono- or polysubstituted or unsubstituted;

$R^{05}$ is selected from H provided with a protective group; $C_{3-8}$ cycloalkyl, aryl or heteroaryl, each being unsubstituted or mono- or polysubstituted; $-CHR^{11}R^{12}$, $-CHR^{11}-CH_2R^{12}$, $-CHR^{11}-CH_2-CH_2R^{12}$, $-CHR^{11}-CH_2-CH_2-CH_2R^{12}$, $-C(Y)R^{12}$, $-C(Y)-CH_2R^{12}$, $-C(Y)-CH_2-CH_2R^{12}$ or $-C(Y)-CH_2-CH_2-CH_2R^{12}$ where $Y=H_2$, where $R^{11}$ is selected from H, $C_{1-7}$ alkyl, saturated or unsaturated, branched or unbranched, mono- or polysubstituted or unsubstituted;

and where $R^{12}$ is selected from

H; $C_{3-8}$ cycloalkyl, aryl or heteroaryl, each being unsubstituted or mono- or polysubstituted, or $R^{04}$ and $R^{05}$ together form a heterocyclic compound with between 3 and 8 atoms in the ring, saturated or unsaturated; mono- or polysubstituted or unsubstituted, and $S^1$ and $S^2$ are independently selected from protective groups or together denote a protective group, preferably monoacetal.

For both processes A it is particularly advantageous if the protective groups at H in $R^{01}$, $R^{02}$, $R^{04}$, $R^{05}$ and/or $R^{06}$ are selected from alkyl, benzyl or carbamates, for example FMOC, Z or Boc.

For the main process A it is particularly advantageous if the reductive amination in step d takes place in the presence of ammonium formate, ammonium acetate or $NaCNBH_3$.

For the main process A it is particularly advantageous if instead of the reductive amination with $HNR^{04}R^{05}$ in step d, compound IV is reacted with hydroxylamine and reduced after oxime formation.

For the main process A it is particularly advantageous if the irradiation in step b lasts between 5 and 7 h and/or takes place at room temperature and/or in a saturated acetylene atmosphere and/or under protective gas.

For the alternative process A it is particularly advantageous if the irradiation in step c lasts between 5 and 7 h and/or takes place at room temperature and/or in a saturated acetylene atmosphere and/or under protective gas.

Also suitable is a process for the production of a substituted 2-pyridine cyclohexane-1,4-diamine compound according to the invention, referred to below as main process B, comprising the following steps:

a. a cyclohexane-1,4-dione protected with groups $S^1$ and $S^2$ according to formula II is reacted in the presence of a compound having the formula $HNR^{01}R^{02}$ with a cyanide, preferably potassium cyanide, to give a protected N-substituted 1-amino-4-oxocyclohexane carbonitrile compound according to formula III;

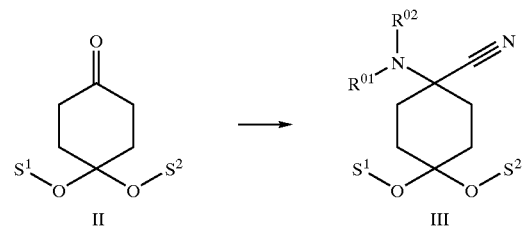

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, b. the aminonitrile according to formula III is reacted with organometallic reagents, preferably Grignard or organolithium reagents, having the formula metal-2-pyridine-$R^3$, such that a compound according to formula IVa is produced;

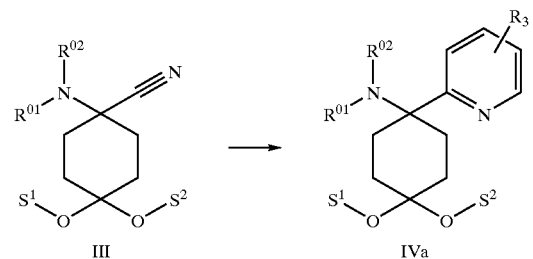

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, c. the protective groups $S^1$ and $S^2$ are eliminated at the compound according to formula IVa such that a tetrasubstituted 4-aminocyclohexanone compound according to formula IV is produced;

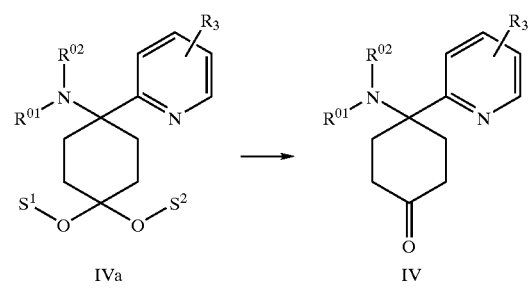

acylation, alkylation or sulfonation is then optionally performed in any sequence and optionally more than once and/or in the case of compounds where $R^{01}$ and/or $R^{02}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{06}$=H, a protective group is introduced at least once and acylation, alkylation or sulfonation optionally performed, d. the tetrasubstituted 4-aminocyclohexanone compound according to formula IVa is reductively aminated with a compound having the formula $HNR^{04}R^{05}$ such that a 2-pyridine cyclohexane-1,4-diamine compound according to formula V is produced;

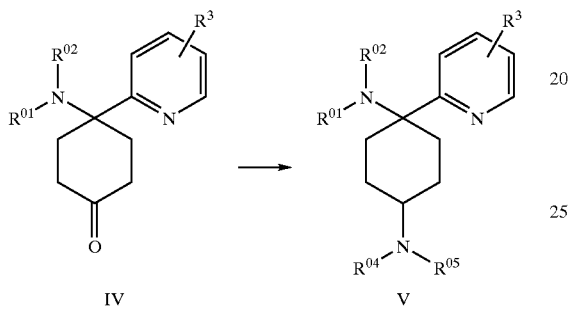

IV    V acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}$=H, a protective group is introduced at least once and acylation, alkylation or sulfonation optionally performed, until a compound according to formula I is produced, wherein $R^1$, $R^2$, $R^4$ and $R^5$ have the meaning given for the compounds according to the invention according to formula I and $R^{01}$ and $R^{02}$ are independently selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

$R^{04}$ is selected from H, H provided with a protective group; $C_{1-8}$ alkyl, saturated or unsaturated, branched or unbranched, mono- or polysubstituted or unsubstituted;

$R^{05}$ is selected from H, H provided with a protective group; $C_{3-8}$ cycloalkyl, aryl or heteroaryl, each being unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where $Y=H_2$, where $R^{11}$ is selected from
H, $C_{1-7}$ alkyl, saturated or unsaturated, branched or unbranched, mono- or polysubstituted or unsubstituted;

and where $R^{12}$ is selected from
H; $C_{3-8}$ cycloalkyl, aryl or heteroaryl, each being unsubstituted or mono- or polysubstituted, or $R^{04}$ and $R^{05}$ together form a heterocyclic compound with between 3 and 8 atoms in the ring, saturated or unsaturated; mono- or polysubstituted or unsubstituted, and $S^1$ and $S^2$ are independently selected from protective groups or together denote a protective group, preferably monoacetal.

The term alkylation here also includes a reductive amination, since it leads to the same result.

The invention also preferably provides a process for the production of a substituted 2-pyridine cyclohexane-1,4-diamine compound according to the invention, referred to below as alternative process B, comprising the following steps:

a. a cyclohexane-1,4-dione protected with groups $S^1$ and $S^2$ according to formula II is reductively aminated with a compound having the formula $HNR^{04}R^{05}$ such that a 4-aminocyclohexanone compound according to formula VI is produced;

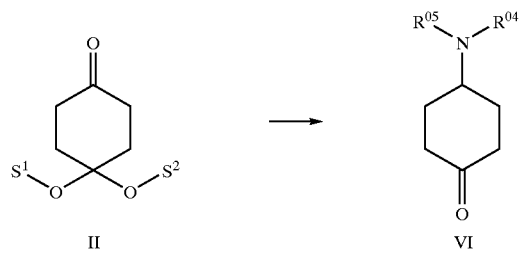

II    VI acylation, alkylation or sulfonation is then optionally performed in any sequence and optionally more than once and/or in the case of compounds where $R^{04}$ and/or $R^{05}$=H protected by a protective group, a protective group is eliminated at least once and acylation, alkylation or sulfonation optionally performed and/or in the case of compounds where $R^{04}$ and/or $R^{05}$=H, a protective group is introduced at least once and acylation, alkylation or sulfonation optionally performed, b. the 4-aminocyclohexanone compound according to formula VI is reacted in the presence of a compound having the formula $HNR^{01}R^{02}$ with cyanide, preferably potassium cyanide, to give a cyclohexanone nitrile compound having formula VII,

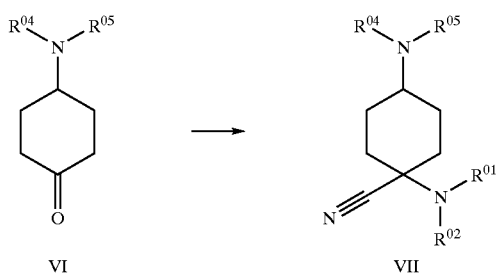

VI → VII acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}$=H, a protective group is introduced at least once and acylation, alkylation or sulfonation optionally performed, c. the cyclohexanone nitrile compound having formula VII is reacted with organometallic reagents, preferably Grignard or organolithium reagents, having the formula metal-2-pyridine-$R^3$ and the protective groups $S^1$ and $S^2$ finally eliminated such that a 2-pyridine cyclohexane-1,4-diamine compound according to formula V is produced,

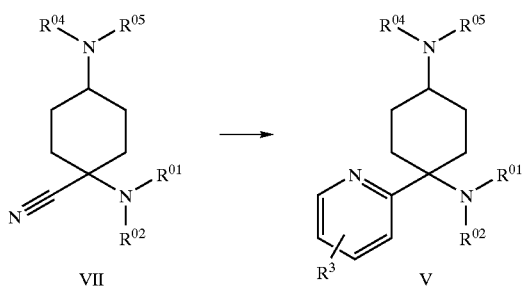

VII →  V acylation, alkylation or sulfonation is then optionally performed in any sequence and optionally more than once and/or in the case of compounds where $R^{01}$ and/or $R^{02}$ and/or $R^{04}$ and/or $R^{05}$ and/or $R^{06}$=H protected by a protective group, a protective group is eliminated at least once and acylation, alkylation or sulfonation optionally performed and/or in the case of compounds where $R^{01}$ and/or $R^{02}$ and/or $R^{04}$ and/or $R^{05}$ and/or $R^{06}$=H, a protective group is introduced at least once and acylation, alkylation or sulfonation optionally performed, until a compound according to formula I is produced, wherein $R^1$, $R^2$, $R^4$ and $R^5$ have the meaning given for the compounds according to the invention according to formula I and $R^{01}$ and $R^{02}$ are independently selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

or the radicals $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from H; H provided with a protective group; $C_{1-8}$ alkyl or $C_{3-8}$ cycloalkyl, each being saturated or unsaturated, branched or unbranched, mono- or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted;

$R^{04}$ is selected from H, H provided with a protective group; $C_{1-8}$ alkyl, saturated or unsaturated, branched or unbranched, mono- or polysubstituted or unsubstituted;

$R^{05}$ is selected from H provided with a protective group; $C_{3-8}$ cycloalkyl, aryl or heteroaryl, each being unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$ or —$C(Y)$—$CH_2$—$CH_2$—$CH_2R^{12}$ where Y=$H_2$, where $R^{11}$ is selected from H, $C_{1-7}$ alkyl, saturated or unsaturated, branched or unbranched, mono- or polysubstituted or unsubstituted;

and where $R^{12}$ is selected from

H; $C_{3-8}$ cycloalkyl, aryl or heteroaryl, each being unsubstituted or mono- or polysubstituted, or $R^{04}$ and $R^{05}$ together form a heterocyclic compound with between 3 and 8 atoms in the ring, saturated or unsaturated; mono- or polysubstituted or unsubstituted, and $S^1$ and $S^2$ are independently selected from protective groups or together denote a protective group, preferably monoacetal.

For both processes B it is further preferable that the protective groups at H in $R^{01}$, $R^{02}$, $R^{04}$, $R^{05}$ and/or $R^{06}$ are selected from alkyl, benzyl or carbamates, for example FMOC, Z or Boc.

For the main process B it is preferable if the reductive amination in step d takes place in the presence of ammonium formate, ammonium acetate or $NaCNBH_3$.

For the main process B it is also a particularly advantageous embodiment if instead of the reductive amination with $HNR^{04}R^{05}$ in step d, compound IV is reacted with hydroxylamine and reduced after oxime formation.

It is equally advantageous for the alternative process B if in step b the radical $R^{01}$ in formula $HNR^{01}R^{02}$ is H, the reaction with cyanide occurs with TMSCN and a protective group is then optionally introduced at $R^{01}$.

The invention will be described in further detail below with reference to illustrative working examples, without being restricted to them.

EXAMPLES

The following examples are intended to illustrate the invention in more detail but do not restrict the general concepts of the invention.

The yields of the compounds produced are not optimized. All temperatures are uncorrected.

The reference "ether" denotes diethyl ether, "EE" denotes ethyl acetate and "DCM" dichloromethane. The reference "equivalents" denotes substance amount equivalents, "mp" denotes melting point or melting range, "RT" denotes room temperature, "vol. %" percent by volume, "m %" percent by mass and "M" is a measure of concentration in mole/liter.

Silica gel 60 (0.040–0.063 mm) from E. Merck, Darmstadt, was used as the stationary phase for column chromatography. Examinations by thin-layer chromatography were performed with HPTLC chromatoplates, silica gel 60 F 254, from E. Merck, Darmstadt.

The mixing ratios for mobile solvents for chromatographic examinations are always given in volume/volume.

Example 1

N'-benzyl-N,N-dimethyl-1-phenyl cyclohexane-1,4-diamine hydrochloride, non-polar diastereomer Example 1

N-(4-dimethylamino-4-pyridin-2-yl cyclohexyl)-N-[2-(1H-indol-3-yl)ethyl] acetamide dihydrochloride, non-polar diastereomer 200 ml methanol, 1680 ml aqueous dimethylamine solution (40 m %), 303 g dimethylamine hydrochloride and 200 g potassium cyanide were added to 200 g 1,4-dioxaspiro [4.5]decan-8-one and stirred for approximately 65 hours. The resulting white suspension was extracted four times with 800 ml ether each time, the combined extracts concentrated to low volume, the residue taken up in approximately 500 ml dichloromethane and the phases separated. The organic phase was dried over sodium sulfate, filtered and concentrated to low volume. 265 g 8-dimethylamino-1,4-dioxaspiro[4.5]decane-8-carbonitrile were obtained as a white solid.

A solution of 4.5 g 8-dimethylamino-1,4-dioxaspiro[4.5] decane-8-carbonitrile, 50 mg cyclopentadienyl cycloocta-1, 5-diene cobalt (I) [cpCo(cod)] and 100 ml toluene were transferred into the reaction vessel in a protective gas/acetylene counterflow. After saturation with acetylene the reaction solution was irradiated for a period of 6 hours at a temperature of 25° C. with vigorous stirring. The reaction was interrupted by switching off the lamps and air supply, and the reaction solution was concentrated to low volume. The resulting crude product (5.47 g) was taken up in a mixture of water (8.7 ml) and concentrated hydrochloric acid (15 ml) and stirred overnight at room temperature. To recover the product it was washed with diethyl ether (3×100 ml), the phases separated, the aqueous phase alkalified with 32 percent by mass of sodium hydroxide solution, extracted with dichloromethane (3×100 ml), the combined extracts dried ($Na_2SO_4$), filtered and concentrated to low volume. 3.72 g 4-dimethylamino-4-pyridin-2-yl cyclohexanone were obtained.

Acetic acid (0.448 ml) was added to a solution of 4-dimethylamino-4-pyridin-2-yl cyclohexanone (873 mg) and tryptamine (640 mg) in dry tetrahydrofuran (40 ml) and anhydrous 1,2-dichloroethane (10 ml) and stirred for 15 min. Following addition of sodium triacetoxyboron hydride (1.2 g) the reaction mixture was stirred for three days under argon at room temperature. To recover the product the solvent was removed in vacuo, the residue taken up in 1N sodium hydroxide solution (40 ml) and diethyl ether (40 ml), the phases separated, the aqueous phase extracted with diethyl ether (2×30 ml), the organic phases combined, dried and concentrated to low volume. The resulting raw product was separated by column chromatography on silica gel with methanol and methanol/ammonia (100:1). The non-polar diastereoisomer of N'-[2-(1H-indol-3-yl)ethyl]-N,N-dimethyl-1-pyridin-2-yl cyclohexane-1,4-diamine was obtained as a white solid (617 mg; mp 150–152° C.).

N'-[2-(1H-indol-3-yl)ethyl]-N,N-dimethyl-1-pyridin-2-yl cyclohexane-1,4-diamine (250 mg) was dissolved in dry pyridine (5 ml), acetic anhydride (0.64 ml) was added and the mixture was stirred for 22 hours at room temperature. Some ice was added to the reaction mixture and it was then concentrated to low volume. The residue was taken up in 1M sodium hydroxide solution (20 ml) and ethyl acetate (20 ml) and stirred. A white solid was left behind, which could be suction filtered (86 mg). The aqueous phase of the filtrate was extracted with ethyl acetate (2×20 ml). The combined organic extracts were concentrated to low volume after drying. The residue obtained in this way was identical to the solid obtained earlier. Both substances were combined. 219 mg N-(4-dimethylamino-4-pyridin-2-yl cyclohexyl)-N-[2-(1H-indol-3-yl)ethyl] acetamide were obtained (mp 209–210° C.), of which 195 mg were dissolved in 2-butanone (25 ml) with gentle heating to 40° C. and converted into the corresponding dihydrochloride with chlorotrimethyl silane (0.303 ml) (white solid; 219 mg; mp 244–247° C.).

Example 2

N'-[2-(1H-indol-3-yl)ethyl]-N,N-dimethyl-1-pyridin-2-yl cyclohexane-1,4-diamine trihydrochloride, non-polar diastereomer The N'-[2-(1H-indol-3-yl)ethyl]-N,N-dimethyl-1-pyridin-2-yl cyclohexane-1,4-diamine obtained according to example 1 (342 mg) was dissolved in 2-butanone (20 ml) and converted to the corresponding trihydrochloride with chlorotrimethyl silane (0.59 ml) (beige-coloured solid; 408 mg).

Example 3

N'-[2-(1H-indol-3-yl)ethyl]-N,N-dimethyl-1-pyridin-2-yl cyclohexane-1,4-diamine trihydrochloride, polar diastereoisomer As described for example 1, 171 mg of the polar diastereoisomer of N'-[2-(1H-indol-3-yl)ethyl]-N,N-dimethyl-1-pyridin-2-yl cyclohexane-1,4-diamine were also obtained, dissolved in 2-butanone (20 ml) and converted into the corresponding trihydrochloride with chlorotrimethyl silane (0.297 ml) (171 mg beige solid, mp 225–230° C.).

Example 4

N'-[2-(1H-indol-3-yl)ethyl]-N,N-dimethyl-1-pyridin-2-yl cyclohexane-1,4-diamine trihydrochloride, non-polar diastereoisomer The hydrochloride of L-tryptophane methyl ester (1.01 g) was stirred vigorously with 1,2-dichloroethane (20 ml) and saturated $NaHCO_3$ solution (20 ml) for 15 min, and the aqueous phase was extracted with 1,2-dichloroethane (2×20 ml). After drying with $Na_2SO_4$ the organic phase was concentrated to 40 ml, and 4-dimethylamino-4-pyridin-2-yl cyclohexanone (873 mg) was added under argon. Glacial acetic acid (0.448 ml) and $Na_2SO_4$ (2 g) were added to the clear solution. After a reaction time of 15 min $NaBH(OAc)_3$ (1.2 g) was added to the reaction mixture, and it was stirred for four days at room temperature. To recover the product saturated $NaHCO_3$ solution (40 ml) was added to the mixture, and it was stirred for 15 min. The aqueous phase was extracted with dichloromethane (2×30 ml), and the combined organic phases were concentrated to low volume after drying to obtain a light-brown oil. Chromatographic separation of the mixture of substances on silica gel was performed with ethyl acetate/methanol (4:1) and methanol. The non-polar product (820 mg light oily compound) was dissolved in 2-butanone (50 ml) and converted to the trihydrochloride with chlorotrimethyl silane (1.22 ml) (719 mg white hygroscopic solid; $[\alpha]_D^{20}$=19.85 (MeOH, c=1.33)).

Example 5

(S)-2-(4-dimethylamino-4-pyridin-2-yl cyclohexylamino)-3-(1H-indol-3-yl) methyl propionate trihydrochloride, polar diastereomer As described in example 4, 284 mg of the polar diastereoisomer of (S)-2-(4-dimethylamino-4-pyridin-2-yl cyclohexylamino)-3-(1H-indol-3-yl) methyl propionate were also obtained, dissolved in 2-butanone (15 ml) and converted to the corresponding trihydrochloride with chlorotrimethyl silane (0.43 ml) (171 mg white solid; mp 170–175° C.; $[\alpha]_D^{20}$=17.61 (MeOH, c=1.45)).

Example 6

(S)-2-(4-dimethylamino-4-pyridin-2-yl cyclohexylamino)-3-(1H-indol-3-yl) propionic acid dihydrochloride, non-polar diastereomer 1.7N KOH (8.8 ml) was added to a solution of the non-polar diastereoisomer of N'-[2-(1H-indol-3-yl)ethyl]-N,N-dimethyl-1-pyridin-2-yl cyclohexane-1,4-diamine trihydrochloride produced according to example 4 (378 mg) in ethanol (20 ml). After 70 hours it was concentrated to low volume, the remaining yellow oil dissolved in water (10 ml), the aqueous phase washed with ethyl acetate (3×20 ml) and 5.5N HCl (9.0 ml) added. The aqueous phase was concentrated to low volume and the residue digested with ethanol (2×20 ml). The remaining KCl was separated out and the filtrate concentrated to low volume and washed with ether. The dihydrochloride of (S)-2-(4-dimethylamino-4-pyridin-2-yl cyclohexylamino)-3-(1H-indol-3-yl) propionic acid dihydrochloride, non-polar, was obtained in this process (307 mg $[\alpha]_D^{20}$=20.69 (MeOH, c=1.213)).

Example 8

Measurement of ORL1 Binding

The cyclohexane-1,4-diamine compounds corresponding to the formula I were investigated in a receptor binding assay with $^3$H-nociceptin/orphanin FQ with membranes of recombinant CHO-ORL1 cells. This test system was performed according to the method put forward by Ardati et al. (Mol., Pharmacol., 51, 1997, p. 816–824). The concentration of $^3$H-nociceptin/orphanin FQ in these tests was 0.5 nM. The binding assays were performed with 20 μg membrane protein per 200 μl batch in 50 mM hepes, pH 7.4, 10 mM MgCl$_2$ and 1 mM EDTA. Binding to the ORL1 receptor was determined using 1 mg WGA-SPA beads (Amersham-Pharmacia, Freiburg) by incubation of the batch for one hour at room temperature followed by measurement in a Trilux scintillation counter (Wallac, Finland). The affinity is given as the $K_i$ value in μM.

| Example | ORL1 Ki/μM |
|---------|------------|
| 1 | 0.18 |
| 2 | 0.013 |
| 3 | 0.34 |
| 4 | 0.093 |
| 5 | 0.47 |
| 6 | 0.28 |

Example 9

Analgesia Testing in the Tail Flick Test in Mice

The mice were placed individually into a test cage and the base of the tail exposed to a focused beam of heat from an electric lamp (tail flick type 50/08/1.bc, Labtec, Dr. Hess). The lamp intensity was adjusted so that the time from switching on the lamp to the sudden flicking away of the tail (pain latency) for untreated mice was 3 to 5 seconds. Before administration of the solutions containing the compound according to the invention or the comparative solutions the mice were pre-tested twice within five minutes and the mean of these measurements calculated as the pre-test mean.

The solutions of the compound according to the invention corresponding to the formula I and the comparative solutions were then administered intravenously. The pain was measured at 10, 20, 40 and 60 minutes after intravenous administration. The analgesic activity was determined as the increase in pain latency (% of the maximum possible antinociceptive effect) according to the formula below:

% MPE=$[(T_1-T_0)/(T_2-T_0)]\times100$

In this formula the time $T_0$ is the latency time before administration, the time $T_1$ the latency time after administration of the active ingredient combination and the time $T_2$ the maximum exposure time (12 seconds).

The compounds according to the invention that were examined displayed an analgesic effect. The results of selected tests are summarized in the following table.

TABLE

| Example no. | % MPE in comparison to control group |
|-------------|--------------------------------------|
| 1 | 71 (10) |
| 4 | 91 (10) |

The dose in mg/kg for intravenous administration is given in parentheses.

Example 10

Parenteral solution of a substituted 2-pyridine cyclohexane-1,4-diamine compound according to the invention 38 g of the substituted 2-pyridine cyclohexane-1,4-diamine compounds according to the invention, in this case according to example 1, is dissolved in 1 liter of sterile, injectable water at room temperature and then adjusted to isotonic conditions by addition of anhydrous injectable glucose.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A substituted 2-pyridine cyclohexane-1,4-diamine compound corresponding to formula I

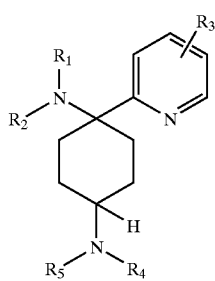

I wherein
$R^1$ and $R^2$ are independently selected from the group consisting of H and $C_{1-8}$ alkyl, saturated or unsaturated, branched or unbranched unsubstituted or, mono- or polysubstituted with at least one F, Cl, Br, I, $NH_2$, SH or OH, or
$R^1$ and $R^2$ together form a ring and denote $CH_2CH_2OCH_2CH_2$, $CH_2CH_2NR^6CH_2CH_2$ or $(CH_2)_{3-6}$, where
  $R^6$ is selected from the group consisting of H and $C_{1-8}$ alkyl, saturated or unsaturated, branched or unbranched, mono- or polysubstituted or unsubstituted;
$R^3$ is selected from the group consisting of H; $C_{1-8}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl and heteroaryl, each being mono- or polysubstituted or unsubstituted; aryl, $C_{3-8}$ cycloalkyl and heteroaryl each bonded via $C_{1-3}$ alkylene and each being mono- or polysubstituted or unsubstituted; SH, OH, F, Cl, I, Br, CN, $NO_2$, $OR^{26}$, and $NR^{27}R^{28}$; where
  $R^{26}$ is selected from the group consisting of $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl and heteroaryl, each being unsubstituted or mono- or polysubstituted with at least one substituent selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH; aryl, $C_{3-8}$ cycloalkyl and heteroaryl each bonded via $C_{1-3}$ alkyl, saturated or unsaturated, and each being unsubstituted or mono- or polysubstituted with at least one substituent selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH;
$R^{27}$ and $R^{28}$ are independently selected from the group consisting of H; $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl and heteroaryl, each being unsubstituted or mono- or polysubstituted with at least one substituent selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH; aryl, $C_{3-8}$ cycloalkyl and heteroaryl each bonded via $C_{1-3}$ alkyl, saturated or unsaturated, and each being unsubstituted or mono- or polysubstituted with at least one substituent selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH; or
$R^{27}$ and $R^{28}$ together denote $CH_2CH_2OCH_2CH_2$, $CH_2CH_2NR^{29}CH_2CH_2$ or $(CH_2)_{3-6}$, where
  $R^{29}$ is selected from the group consisting of H; $C_{1-6}$ alkyl, saturated or unsaturated, branched or unbranched, mono- or polysubstituted or unsubstituted; $C_{3-8}$ cycloalkyl, saturated or unsaturated, mono- or polysubstituted or unsubstituted; aryl and heteroaryl, each being unsubstituted or mono- or polysubstituted with at least one substituent selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH; aryl, $C_{3-8}$ cycloalkyl and heteroaryl each bonded via $C_{1-3}$ alkyl, satured or unsatured, and each being unsubstituted or mono- or polysubstituted with a least one substituted selected from the group consisting of F, Cl, Br, I, $NH_2$, $NO_2$, $CF_3$, $CHF_2$, $CH_2F$, $CH_3$, $C_2H_5$, $C_3H_7$, $C_4H_9$, $OCF_3$, $OCHF_2$, $OCH_2F$, $OCH_3$, $OC_2H_5$, $OC_3H_7$, $OC_4H_9$, SH and OH;
$R^4$ is selected from the group consisting of H; $C_{1-8}$ alkyl, saturated or unsaturated, branched or unbranched, mono- or polysubstituted or unsubstituted; $C(X)R^7$; $C(X)NR^7R^8$; $C(X)OR^9$; $C(X)SR^9$; and $S(O_2)R^9$, where X=O or S,
  $R^7$ is selected from the group consisting of H; $C_{1-8}$ alkyl and $C_{3-8}$ cycloalkyl, each being saturated or unsaturated, branched or unbranched, mono- or polysubstituted or unsubstituted; aryl and heteroaryl, each being unsubstituted or mono- or polysubstituted; aryl, $C_{3-8}$ cycloalkyl and heteroaryl, each bonded via a saturated or unsaturated, branched or unbranched, substituted or unsubstituted $C_{1-4}$ alkyl group, and each being unsubstituted or mono- or polysubstituted;
  $R^8$ is H or $C_{1-4}$ alkyl, saturated or unsaturated, branched or unbranched, mono- or polysubstituted or unsubstituted, or
  $R^7$ and $R^8$ together form a ring and denote $CH_2CH_2OCH_2CH_2$, $CH_2CH_2NR^{10}CH_2CH_2$ or $(CH_2)_{3-6}$, where
    $R^{10}$ is selected from the group consisting of H; $C_{1-8}$ alkyl and $C_{3-8}$ cycloalkyl, each being saturated or unsaturated, branched or unbranched, mono- or polysubstituted or unsubstituted; aryl and heteroaryl, each being mono- or polysubstituted or unsubstituted; and aryl, $C_{3-8}$ cycloalkyl and heteroaryl, each bonded via $C_{1-3}$ alkylene, and each being mono- or polysubstituted or unsubstituted; and $R^9$ is selected from the group consisting of $C_{1-8}$ alkyl, $C_{3-8}$ cycloalkyl, each being saturated or unsaturated, branched or unbranched, mono- or polysubstituted or unsubstituted; aryl, heteroaryl, each being unsubstituted or mono- or polysubstituted; and aryl, $C_{3-8}$ cycloalkyl or heteroaryl bonded via a saturated or unsaturated, branched or unbranched, substituted or unsubstituted $C_{1-4}$ alkyl group, each being unsubstituted or mono- or polysubstituted;

$R^5$ is selected from the group consisting of $C_{3-8}$ cycloalkyl, aryl, heteroaryl, each being unsubstituted or mono- or polysubstituted; —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$-$CH_2R^{12}$ and —$C(Y)$—$CH_2$—$CH_2$—$CH_2R^{12}$, where Y=O, S or $H_2$, where $R^{11}$ is selected from the group consisting of H; $C_{1-7}$ alkyl, saturated or unsaturated, branched or unbranched, mono- or polysubstituted or unsubstituted; and $C(O)O|C_{1-16}$ alkyl, saturated or unsaturated, branched or unbranched, mono- or polysubstituted or unsubstituted; and $R^{12}$ is selected from the group consisting of H, $C_{3-8}$ cycloalkyl, aryl and heteroaryl, wherein the $C_{3-8}$ cycloalkyl, aryl and heteroaryl may be unsubstituted or mono- or polysubstituted, or $R^4$ and $R^5$ together form a heterocyclic ring containing from 3 to 8 atoms, saturated or unsaturated, mono- or polysubstituted or unsubstituted, which can optionally be condensed with other rings, wherein said compound is in the form of a racemate, a pure stereoisomer, a mixture of stereoisomers in any mixing ratio, a free base, a salt or a solvate.

2. A compound according to claim 1, wherein $R^1$ and $R^2$ are independently selected from the group consisting of H and $C_{1-4}$ alkyl, saturated or unsaturated, branched or unbranched, mono- or polysubstituted or unsubstituted, or $R^1$ and $R^2$ together form a ring and denote $(CH_2)_{4-5}$.

3. A compound according to claim 2, wherein $R^1$ and $R^2$ are independently selected from methyl and ethyl, or $R^1$ and $R^2$ together form a ring and denote $(CH_2)_5$.

4. A compound according to claim 1, wherein $R^3$ is selected from the group consisting of H; $C_{1-8}$ alkyl, each being saturated or unsaturated, branched or unbranched, mono- or polysubstituted or unsubstituted; $C_{3-8}$ cycloalkyl, saturated or unsaturated, mono-or polysubstituted or unsubstituted; aryl or heteroaryl, each being mono- or polysubstituted or unsubstituted; or aryl, $C_{3-8}$ cycloalkyl or heteroaryl bonded via $C_{1-3}$ alkylene, each being mono- or polysubstituted or unsubstituted; SH, OH, F, Cl, I, Br, CN, $NO_2$, $NH_2$, and $OR^{26}$, where $R^{26}$ is $C_{1-6}$ alkyl, saturated or unsaturated, branched or unbranched, mono- or polysubstituted or unsubstituted.

5. A compound according to claim 1, wherein $R^3$ is selected from the group consisting of H; $C_{1-6}$ alkyl, each being saturated or unsaturated, branched or unbranched, mono- or polysubstituted or unsubstituted; SH, OH, F, Cl, I, Br, CN, $NO_2$, $NH_2$, and $OR^{26}$, where $R^{26}$ is selected from $C_{1-6}$ alkyl, saturated or unsaturated, branched or unbranched, mono- or polysubstituted or unsubstituted.

6. A compound according to claim 5, wherein $R^3$ is H.

7. A compound according to claim 1, wherein $R^4$ is selected from the group consisting of H, $C(X)R^7$, $C(X)NR^7R^8$, $C(X)OR^9$, $C(X)SR^9$ and $S(O_2)R^9$, where X=O or S.

8. A compound according to claim 7, wherein $R^4$ is selected from the group consisting of H, $C(X)R^7$, $C(X)NR^7R^8$ and $C(X)OR^9$, where X=O.

9. A compound according to claim 8, wherein $R^4$ is H or $C(O)R^7$, where $R^7$ is H or $C_{1-8}$ alkyl, saturated or unsaturated, branched or unbranched, mono- or polysubstituted or unsubstituted.

10. A compound according to claim 9, where $R^7$ is H or $C_{1-3}$ alkyl, saturated, unsubstituted, branched or unbranched.

11. A compound according to claim 10, wherein $R^7$ is $CH_3$.

12. A compound according to claim 1, wherein $R^4$ and $R^5$ together form an N-containing heterocyclic ring containing from 3 to 8 atoms, saturated or unsaturated; mono- or polysubstituted or unsubstituted.

13. A compound according to claim 12, wherein said N-containing heterocyclic ring contains from 5 to 7 atoms, including in addition to said N, zero or 1 other heteroatom selected from the group consisting of N, S and O.

14. A compound according to claim 12, wherein the heterocyclic ring formed by $R^4$ and $R^5$ together is condensed with at least one other ring.

15. A compound according to claim 14, wherein said at least one other ring comprises an aromatic or heteroaromatic ring.

16. A compound according to claim 15, wherein the aromatic or heteroaromatic ring is condensed at least one further aromatic or heteroaromatic ring.

17. A compound according to claim 14, wherein the heterocyclic ring formed by $R^4$ and $R^5$ together is condensed with one or two other rings.

18. A compound according to claim 14, wherein the heterocyclic ring formed by $R^4$ and $R^5$ together is condensed with two other rings such that $R^4$ and $R^5$ together denote

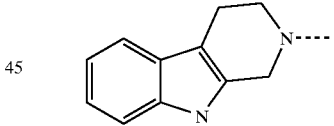

19. A compound according to claim 1, wherein $R^4$ is H or $C_{1-8}$ alkyl, saturated or unsaturated, branched or unbranched, mono- or polysubstituted or unsubstituted.

20. A compound according to claim 19, wherein $R^4$ is H or $C_{1-6}$ alkyl, saturated or unsaturated, branched or unbranched, mono- or polysubstituted or unsubstituted.

21. A compound according to claim 20, wherein $R^4$ is H or saturated, unbranched and unsubstituted $C_{1-3}$ alkyl.

22. A compound according to claims 1, wherein $R^5$ is selected from the group consisting of $C_{3-8}$ cycloalkyl, aryl and heteroaryl, each being unsubstituted or mono- or polysubstituted.

23. A compound according to claim 22, wherein $R^5$ is selected from the group consisting of cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl, and quinazolinyl, each being unsubstituted or mono- or polysubstituted.

24. A compound according to claim 23, wherein $R^5$ is selected from the group consisting of cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl and pyrimidyl, each being unsubstituted or mono- or polysubstituted.

25. A compound according to claim 1, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$CHR^{11}$—$CH_2$—$CH_2$—$CH_2R^{12}$, —$C(Y)R^{12}$, —$C(Y)$—$CH_2R^{12}$, —$C(Y)$—$CH_2$—$CH_2R^{12}$, and —$C(Y)$—$CH_2$—$CH_2$—$CH_2R^{12}$, where Y=O, S or $H_2$.

26. A compound according to claim 25, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$C(Y)R^{12}$, —$C(Y)$—$CH_2R^{12}$, and —$C(Y)$—$CH_2$—$CH_2R^{12}$, where Y=O or S.

27. A compound according to claim 26, wherein $R^5$ is selected from the group consisting of —$CHR^{11}R^{12}$, —$CHR^{11}$—$CH_2R^{12}$, —$CHR^{11}$—$CH_2$—$CH_2R^{12}$, —$C(Y)R^{12}$, and —$C(Y)$—$CH_2R^{12}$, where Y=O.

28. A compound according to claim 25, wherein $R^{11}$ is selected from the group consisting of H; $C_{1-4}$ alkyl, saturated or unsaturated, branched or unbranched, mono- or polysubstituted or unsubstituted; and C(O)O¦ $C_{1-4}$ alkyl, saturated or unsaturated, branched or unbranched, mono- or polysubstituted or unsubstituted.

29. A compound according to claim 28, wherein $R^{11}$ is selected from the group consisting of H; $C_{1-4}$ alkyl, saturated or unsaturated, branched or unbranched, mono- or polysubstituted or unsubstituted; and C(O)O¦ $C_{1-2}$ alkyl, saturated, unbranched, mono- or polysubstituted or unsubstituted.

30. A compound according to claim 29, wherein $R^{11}$ is selected from the group consisting of H, $CH_3$, $C_2H_5$, and C(O)O¦$CH_3$.

31. A compound according to claim 25, wherein $R^{12}$ is selected from the group consisting of $C_{3-8}$ cycloalkyl, aryl and heteroaryl, each being unsubstituted or mono- or polysubstituted.

32. A compound according to claim 31, wherein $R^{12}$ is selected from the group consisting of cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl, and quinazolinyl, each being unsubstituted or mono- or polysubstituted.

33. A compound according to claim 32, wherein $R^{12}$ is selected from the group consisting of cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, and pyrimidyl, each being unsubstituted or mono- or polysubstituted.

34. A compound according to claim 1, selected from the group consisting of:
- N-(4-dimethylamino-4-pyridin-2-yl cyclohexyl)-N-[2-(1H-indol-3-yl)ethyl] acetamide dihydrochloride, non-polar diastereoisomer;
- N'-[2-(1H-indol-3-yl)ethyl]-N,N-dimethyl-1-pyridin-2-yl cyclohexane-1,4-diamine trihydrochloride, non-polar diastereoisomer;
- N'-[2-(1H-indol-3-yl)ethyl]-N,N-dimethyl-1-pyridin-2-yl cyclohexane-1,4-diamine trihydrochloride, polar diastereoisomer;
- (S)-2-(4-dimethylamino-4-pyridin-2-yl cyclohexylamino)-3-(1H-indol-3-yl) methyl propionate trihydrochloride, non-polar diastereoisomer;
- (S)-2-(4-dimethylamino-4-pyridin-2-yl cyclohexylamino)-3-(1H-indol-3-yl) methyl propionate trihydrochloride, polar diastereoisomer; and
- (S)-2-(4-dimethylamino-4-pyridin-2-yl cyclohexylamino)-3-(1H-indol-3-yl) propionic acid dihydrochloride, non-polar diastereoisomer in the form of a racemate, a pure stereoisomer, a mixture of diastereoisomers in any desired mixing ratio, a free base, a salt or a solvate.

35. A compound according to claim 1, wherein said compound is in the form of a pure enantiomer or diastereoisomer.

36. A compound according to claim 1, wherein said compound is in the form of a mixture of enantiomers or diastereoisomers.

37. A compound according to claim 1, wherein said compound is in the form of a salt with a physiologically compatible acid.

38. A compound according to claim 1, wherein said compound is in the form of a hydrate.

39. A pharmaceutical composition comprising at least one compound according to claim 1 and at least one carrier, adjuvant or another active substance selected from the group consisting of an opioid and an anaesthetic.

40. A pharmaceutical composition according to claim 39, comprising said compound and an opioid or an anaesthetic.

41. A pharmaceutical composition according to claim 40, comprising said compound and morphine or an anaesthetic selected from the group consisting of hexobarbital and halothane.

42. A method of treating pain in a patient, said method comprising administering to said patient an effective pain treating amount of at least one compound according to claim 1.

43. A method according to claim 42, wherein said pain is acute pain, neuropathic pain, or chronic pain.

44. A process for producing a compound according to claim 1 wherein $R^3$=H, said process comprising the steps of:
a) reacting a cyclohexane-1,4-dione protected with groups $S^1$ and $S^2$ according to formula II with a cyanide in the presence of a compound having the formula $HNR^{01}R^{02}$ to produce a protected N-substituted 1-amino-4-oxo-cyclohexane carbonitrile compound corresponding to formula III

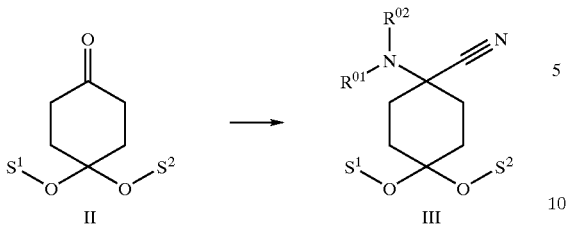

and then optionally acylating, alkylating or sulfonating at least once in any sequence, or if at least one of $R^{01}$, $R^{02}$, and $R^{06}$=H protected by a protective group, eliminating at least one protective group and then optionally acylating, alkylating or sulfonating, or if at least one of $R^{01}$, $R^{02}$, and $R^{06}$=H, introducing at least one H-protective group and then optionally acylating, alkylating or sulfonating, b) contacting the aminonitrile of formula III with cyclopentadienyl cyclooctα-1,5-diene cobalt(I) [cpCo(cod)] and irradiating under acetylene to produce a compound corresponding to formula IVa

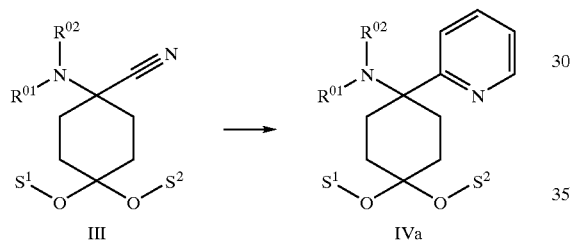

and then optionally acylating, alkylating or sulfonating at least once in any sequence, or if at least one of $R^{01}$, $R^{02}$, and $R^{06}$=H protected by a protective group, eliminating at least one protective group and then optionally acylating, alkylating or sulfonating, or if at least one of $R^{01}$, $R^{02}$, and $R^{06}$=H, introducing at least one H-protective group and then optionally acylating, alkylating or sulfonating, c) eliminating the protective groups $S^1$ and $S^2$ from the compound of formula IVa to produce a tetrasubstituted 4-aminocyclohexanone compound corresponding to formula IV

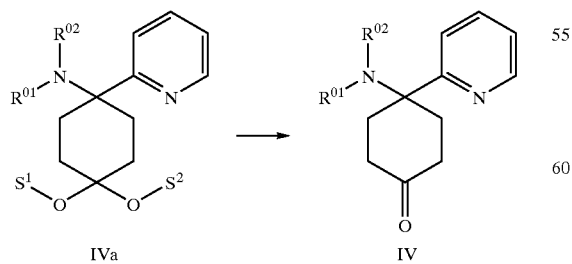

and then optionally acylating, alkylating or sulfonating at least once in any sequence, or if at least one of $R^{01}$, $R^{02}$, and $R^{06}$=H protected by a protective group, eliminating at least one protective group and then optionally acylating, alkylating or sulfonating, or if at least one of $R^{01}$, $R^{02}$, and $R^{06}$=H, introducing at least one H-protective group and then optionally acylating, alkylating or sulfonating, d) reductively aminating the tetrasubstituted 4-aminocyclohexanone compound of formula IVa with a compound having the formula $HNR^{04}R^{05}$ to produce a 2-pyridine cyclohexane-1,4-diamine compound corresponding to formula V

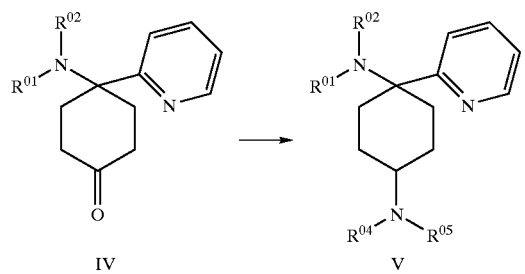

and then optionally acylating, alkylating or sulfonating in any sequence, or if at least one of $R^{01}$, $R^{02}$, $R^{04}$, $R^{05}$, and $R^{06}$=H protected by a protective group, eliminating at least one protective group and then optionally acylating, alkylating or sulfonating, or if at least one of $R^{01}$ $R_{02}$, $R^{04}$, $R^{05}$, and $R^{06}$=H, introducing at least one H-protective group and then optionally acylating, alkylating or sulfonating to produce a compound corresponding to formula I, wherein $R^{01}$ and $R^{02}$ are independently selected from the group consisting of H; H provided with a protective group; $C_{1-8}$ alkyl and $C_{3-8}$ cycloalkyl, each being saturated or unsaturated, branched or unbranched, mono- or polysubstituted or unsubstituted; aryl and heteroaryl, each being mono- or polysubstituted or unsubstituted; and aryl, $C_{3-8}$ cycloalkyl and heteroaryl, each bonded via $C_{1-3}$ alkylene and each being mono- or polysubstituted or unsubstituted; or $R^{01}$ and $R^{02}$ together form a ring and denote $CH_2CH_2OCH_2CH_2$, $CH_2CH_2NR^{06}CH_2CH_2$ or $(CH_2)_{3-6}$, where $R^{06}$ is selected from the group consisting of H; H provided with a protective group; $C_{1-8}$ alkyl and $C_{3-8}$ cycloalkyl, each being saturated or unsaturated, branched or unbranched, mono- or polysubstituted or unsubstituted; aryl and heteroaryl, each being mono- or polysubstituted or unsubstituted; and aryl, $C_{3-8}$ cycloalkyl and heteroaryl, each bonded via $C_{1-3}$ alkylene and each being mono- or polysubstituted or unsubstituted;

$R^{04}$ is selected from from the group consisting of H; H provided with a protective group; and $C_{1-8}$ alkyl, saturated or unsaturated, branched or unbranched, mono- or polysubstituted or unsubstituted;

$R^{05}$ is selected from the group consisting of H; H provided with a protective group; $C_{3-8}$ cycloalkyl, aryl and heteroaryl, each being unsubstituted or mono- or polysubstituted; —$CHR^{11}R^{12}$; —$CHR^{11}$—$CH_2R^{12}$; —$CHR^{11}$—$CH_2$—$CH_2R^{12}$;

—CHR$^{11}$—CH$_2$—CH$_2$—CH$_2$R$^{12}$; —C(Y)R$^{12}$; —C(Y)—CH$_2$R$^{12}$; —C(Y)—CH$_2$—CH$_2$R$^{12}$ and —C(Y)—CH$_2$—CH$_2$—CH$_2$R$^{12}$, where
Y=H$_2$,
R$^{11}$ is selected from the group consisting of H and C$_{1-7}$ alkyl, saturated or unsaturated, branched or unbranched, mono- or polysubstituted or unsubstituted; and
R$^{12}$ is selected from the group consisting of H, and C$_{3-8}$ cycloalkyl, aryl and heteroaryl, each being unsubstituted or mono- or polysubstituted; or
R$^{04}$ and R$^{05}$ together form a heterocyclic ring containing form 3 to 8 atoms, saturated or unsaturated and mono- or polysubstituted or unsubstituted; and
S$^{1}$ and S$^{2}$ are independently selected from protective groups or together denote a protective group.

45. A process according to claim 44, wherein the protective groups at H in at least one of R$^{01}$, R$^{02}$, R$^{04}$, R$^{05}$ and R$^{06}$ are selected from the group consisting of alkyl, benzyl and carbamates.

46. A process according to claim 44, wherein the reductive amination in step d) takes place in the presence of ammonium formate, ammonium acetate or NaCNBH$_3$.

47. A process according to claim 44, wherein instead of the reductive amination with HNR$^{04}$R$^{05}$ in step d), compound IV is reacted with hydroxylamine and reduced after oxime formation.

48. A process according to claim 44, wherein the irradiation in step b) lasts between 5 and 7 hours.

49. A process according to claim 44, wherein the irradiation in step b) takes place at room temperature.

50. A process according to claim 44, wherein the irradiation in step b) takes place in a saturated acetylene atmosphere.

51. A process according to claim 44, wherein the irradiation in step b takes place under a protective gas.

52. A process for producing a compound according to claim 1 wherein R$^{3}$=H, said process comprising the steps of:
a) reductively aminating a cyclohexane-1,4-dione protected with groups S$^{1}$ and S$^{2}$ according to formula II with a compound having the formula HNR$^{04}$R$^{05}$ to produce a 4-aminocyclohexanone compound corresponding to formula VI

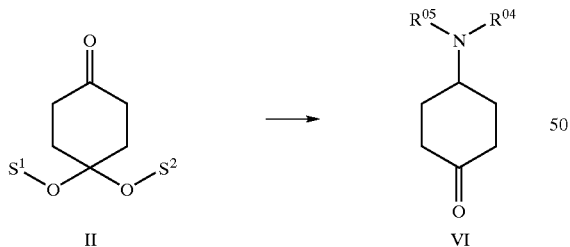

and then optionally acylating, alkylating or sulfonating at least once in any sequence, or
if at least one of R$^{04}$ and R$^{05}$=H protected by a protective group, eliminating at least one protective group and then optionally acylating, alkylating or sulfonating, or
if at least one of R$^{04}$ and R$^{05}$=H, introducing at least one H-protective group and then optionally acylating, alkylating or sulfonating,
b) reacting the 4-aminocyclohexanone compound of formula VI with cyanide in the presence of a compound having the formula HNR$^{01}$R$^{02}$ to produce a cyclohexanone nitrile compound corresponding to formula VII

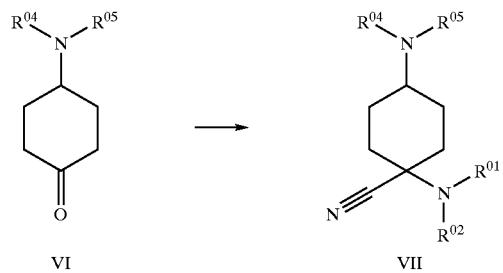

and then optionally acylating, alkylating or sulfonating at least once in any sequence, or
if at least one of R$^{01}$R$^{02}$, R$^{04}$, R$^{05}$ and R$^{06}$=H protected by a protective group, eliminating at least one protective group and then optionally acylating, alkylating or sulfonating, or
if at least one of R$^{01}$, R$^{02}$, R$^{04}$, R$^{05}$ and R$^{06}$=H, introducing at least one H-protective group and then optionally acylating, alkylating or sulfonating,
c) contacting the cyclohexanone nitrile compound of formula VII with cyclopentadienyl cycloocta-1,5-diene cobalt(I) [cpCo(cod)] and irradiating under acetylene to produce a 2-pyridine cyclohexane-1,4-diamine compound corresponding to formula V

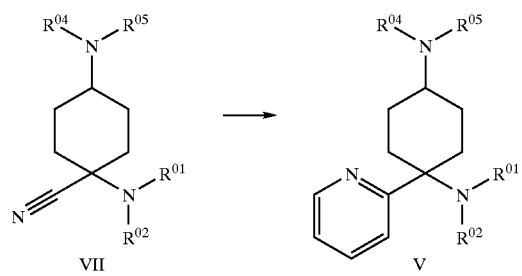

optionally acylating, alkylating or sulfonating at least once in any sequence, or
if at least one of R$^{01}$, R$^{02}$, R$^{04}$, R$^{05}$ and R$^{06}$=H protected by a protective group, eliminating at least one protective group and then optionally acylating, alkylating or sulfonating, or
if at least one of R$^{01}$, R$^{02}$, R$^{04}$, R$^{05}$ and R$^{06}$=H, introducing at least one H-protective group and then optionally acylating, alkylating or sulfonating to produce the compound corresponding to formula I,
wherein
R$^{01}$ and R$^{02}$ are independently selected from the group consisting of H; H provided with a protective group; C$_{1-8}$ alkyl and C$_{3-8}$ cycloalkyl, each being saturated or unsaturated, branched or unbranched, mono- or polysubstituted or unsubstituted; aryl and heteroaryl, each being mono- or polysubstituted or unsubstituted; and aryl, C$_{3-8}$ cycloalkyl and heteroaryl, each bonded via C$_{1-3}$ alkylene and each being mono- or polysubstituted or unsubstituted, or
R$^{01}$ and R$^{02}$ together form a ring and denote CH$_2$CH$_2$OCH$_2$CH$_2$, CH$_2$CH$_2$NR$^{06}$CH$_2$CH$_2$ or (CH$_2$)$_{3-6}$, where $R^{06}$ is selected from the group consisting of H; H provided with a protective group; $C_{1-8}$ alkyl and $C_{3-8}$ cycloalkyl, each being saturated or unsaturated, branched or unbranched, mono- or polysubstituted or unsubstituted; aryl and heteroaryl, each being mono- or polysubstituted or unsubstituted; and aryl, $C_{3-8}$ cycloalkyl and heteroaryl, each bonded via $C_{1-3}$ alkylene and each being mono- or polysubstituted or unsubstituted;

$R^{04}$ is selected from the group consisting of H; H provided with a protective group; and $C_{1-8}$ alkyl, saturated or unsaturated, branched or unbranched, mono- or polysubstituted or unsubstituted;

$R^{05}$ is selected from the group consisting of H provided with a protective group; $C_{3-8}$ cycloalkyl, aryl and heteroaryl, each being unsubstituted or mono- or polysubstituted; —$CHR^{11}R^{12}$; —$CHR^{11}$—$CH_2R^{12}$; —$CHR^{11}$—$CH_2$—$CH_2R^{12}$; —$CHR^{11}$—$CH_2$—$CH_2$—$CH_2R^{12}$; —$C(Y)R^{12}$; —$C(Y)$—$CH_2R^{12}$; —$C(Y)$—$CH_2$—$CH_2R^{12}$, and —$C(Y)$—$CH_2$—$CH_2$—$CH_2R^{12}$, where $Y=H_2$;

$R^{11}$ is selected from the group consisting of H, $C_{1-7}$ alkyl, saturated or unsaturated, branched or unbranched, mono- or polysubstituted or unsubstituted; and $R^{12}$ is selected from the group consisting of H, and $C_{3-8}$ cycloalkyl, aryl and heteroaryl, each being unsubstituted or mono- or polysubstituted, or $R^{04}$ and $R^{05}$ together form a heterocyclic ring containing from 3 to 8 atoms, saturated or unsaturated; mono- or polysubstituted or unsubstituted, and $S^1$ and $S^2$ are independently selected from the group consisting of protective groups or together denote a protective group.

53. A process according to claim 52, wherein the protective groups at H in at least one of $R^{01}$, $R^{02}$, $R^{04}$, $R^{05}$ and $R^{06}$ are selected from the group consisting of alkyl, benzyl and carbamates.

54. A process according to claim 52, wherein the irradiation in step c) lasts between 5 and 7 hours.

55. A process according to claim 52, wherein the irradiation in step c) takes place at room temperature.

56. A process according to claim 52, wherein the irradiation in step c) takes place in a saturated acetylene atmosphere.

57. A process according to claim 52, wherein the irradiation in step c) takes place under a protective gas.

* * * * *